US009576311B2

(12) United States Patent
Xia et al.

(10) Patent No.: US 9,576,311 B2
(45) Date of Patent: Feb. 21, 2017

(54) FOOTCARE PRODUCT DISPENSING KIOSK

(71) Applicant: Bayer HealthCare LLC, Whippany, NJ (US)

(72) Inventors: Bin Xia, Germantown, TN (US); Harold A. Howlett, Horn Lake, TN (US); Charles E. Lundy, Germantown, TN (US)

(73) Assignee: Bayer HealthCare LLC, Whippany, NJ (US)

( * ) Notice: Subject to any disclaimer, the term of this patent is extended or adjusted under 35 U.S.C. 154(b) by 198 days.

(21) Appl. No.: 14/107,526

(22) Filed: Dec. 16, 2013

(65) Prior Publication Data

US 2014/0107966 A1 Apr. 17, 2014

Related U.S. Application Data

(60) Continuation of application No. 13/350,178, filed on Jan. 13, 2012, now abandoned, which is a division of application No. 11/524,745, filed on Sep. 21, 2006, now Pat. No. 8,117,922.

(51) Int. Cl.
*G01D 7/00* (2006.01)
*G06Q 30/06* (2012.01)
*A43D 1/02* (2006.01)
*A43D 1/08* (2006.01)
*A61B 5/103* (2006.01)
(Continued)

(52) U.S. Cl.
CPC ........... *G06Q 30/0631* (2013.01); *A43B 7/24* (2013.01); *A43D 1/02* (2013.01); *A43D 1/022* (2013.01); *A43D 1/08* (2013.01); *A61B 5/1036* (2013.01); *G06Q 20/20* (2013.01)

(58) Field of Classification Search
CPC ...... A43B 7/223; G06Q 30/06; A61B 5/1036; A43D 1/022; A43D 1/08; A43D 1/02
USPC ...................................... 73/862.041–862.046
See application file for complete search history.

(56) References Cited

U.S. PATENT DOCUMENTS

| 2,043,187 A | 6/1936 | Owens |
| 2,975,519 A | 3/1961 | Berlin et al. |
| 3,066,417 A | 12/1962 | Samuels |

(Continued)

FOREIGN PATENT DOCUMENTS

| CA | 2324967 A1 | 5/2002 |
| DE | 19923280 A1 | 11/1999 |

(Continued)

OTHER PUBLICATIONS

Cavanagh, Peter R., et al., "The Arch Index: A Useful Measure From Footprints" published in Journal of Biomechanics, Jan. 1987, pp. 547-551, vol. 20(5), Pergamon Press, New York, NY USA.

(Continued)

*Primary Examiner* — Max Noori
(74) *Attorney, Agent, or Firm* — Thomas C. Blankinship

(57) ABSTRACT

A kiosk apparatus that may select for a person a recommended footcare product based on pressure measurements collected from pressures sensors or calculated biomechanical data estimates. Pressure measurements and calculated biomechanical data estimates may be used to determine if a foot is unshod on the pressure sensor and also group a person into a classified subgroup. The pressure measurement and calculated biomechanical data estimates may also be used to select a recommended footcare product.

1 Claim, 28 Drawing Sheets

(51) Int. Cl.
  *A43B 7/24* (2006.01)
  *G06Q 20/20* (2012.01)

(56) References Cited

U.S. PATENT DOCUMENTS

| | | | |
|---|---|---|---|
| 3,328,882 A | 7/1967 | Blivice | |
| 3,375,586 A | 4/1968 | Kennedy | |
| 3,457,647 A | 7/1969 | Cohen et al. | |
| 3,696,456 A | 10/1972 | Dunham et al. | |
| 4,267,728 A | 5/1981 | Manley et al. | |
| 4,412,364 A | 11/1983 | Mateo | |
| 4,430,645 A | 2/1984 | Eskandry et al. | |
| 4,449,264 A | 5/1984 | Schwartz | |
| 4,510,636 A | 4/1985 | Phillips | |
| 4,517,696 A | 5/1985 | Schartz | |
| 4,520,581 A | 6/1985 | Irwin et al. | |
| 4,538,353 A | 9/1985 | Gardner | |
| 4,555,696 A | 11/1985 | Brown | |
| 4,604,807 A | 8/1986 | Bock et al. | |
| 4,656,344 A | 4/1987 | Mergenthaler et al. | |
| 4,745,290 A | 5/1988 | Frankel et al. | |
| 4,876,758 A | 10/1989 | Rolloff et al. | |
| 4,917,105 A | 4/1990 | Tiitola et al. | |
| 4,972,718 A | 11/1990 | Said et al. | |
| 5,025,476 A | 6/1991 | Gould et al. | |
| 5,128,880 A | 7/1992 | White | |
| 5,164,793 A | 11/1992 | Wolfersberger et al. | |
| 5,168,634 A | 12/1992 | Misevich | |
| 5,195,030 A | 3/1993 | White | |
| 5,203,096 A | 4/1993 | Rosen | |
| 5,206,804 A | 4/1993 | Thies et al. | |
| 5,216,594 A | 6/1993 | White et al. | |
| 5,237,520 A | 8/1993 | White | |
| 5,299,454 A | 4/1994 | Fuglewicz et al. | |
| 5,317,819 A | 6/1994 | Ellis, III | |
| 5,339,252 A | 8/1994 | White et al. | |
| 5,341,819 A | 8/1994 | Hyvarinen | |
| 5,361,133 A | 11/1994 | Brown et al. | |
| 5,394,624 A | 3/1995 | Siepser | |
| 5,586,067 A | 12/1996 | Gross et al. | |
| 5,640,779 A | 6/1997 | Rolloff et al. | |
| 5,659,395 A | 8/1997 | Brown et al. | |
| 5,671,055 A | 9/1997 | Whittlesey et al. | |
| 5,671,362 A | 9/1997 | Cowe et al. | |
| 5,790,256 A | 8/1998 | Brown et al. | |
| 5,822,873 A | 10/1998 | Meilman | |
| 5,957,870 A | 9/1999 | Yamato et al. | |
| 5,979,067 A | 11/1999 | Waters | |
| 5,987,982 A | 11/1999 | Wenman et al. | |
| 5,989,700 A | 11/1999 | Krivopal | |
| 6,160,264 A | 12/2000 | Rebiere | |
| 6,163,971 A | 12/2000 | Humphries, Jr. et al. | |
| 6,219,929 B1 | 4/2001 | Tasker et al. | |
| 6,289,107 B1 | 9/2001 | Borchers et al. | |
| 6,301,805 B1 | 10/2001 | Howlett et al. | |
| 6,331,893 B1 | 12/2001 | Brown et al. | |
| 6,430,831 B1 | 8/2002 | Sundman | |
| 6,498,590 B1 | 12/2002 | Dietz et al. | |
| 6,532,299 B1 | 3/2003 | Sachdeva et al. | |
| 6,550,149 B2 | 4/2003 | Dowdell | |
| 6,563,423 B2 | 5/2003 | Smith | |
| 6,564,465 B1 | 5/2003 | Ward | |
| 6,585,328 B1 | 7/2003 | Oexman et al. | |
| 6,804,571 B2 | 10/2004 | Fullen et al. | |
| 6,823,550 B2 | 11/2004 | Kantro | |
| 6,845,568 B2 | 1/2005 | Ward | |
| 6,909,373 B2 | 6/2005 | Power et al. | |
| 6,939,502 B2 | 9/2005 | Lyden | |
| 6,964,205 B2 | 11/2005 | Papkostas et al. | |
| 7,617,068 B2 | 11/2009 | Tadin et al. | |
| 7,742,633 B2 | 6/2010 | Huang et al. | |
| 8,117,922 B2 | 2/2012 | Xia et al. | |
| 8,170,705 B2 | 5/2012 | Koelling et al. | |
| 2003/0079303 A1 | 5/2003 | Kantro | |
| 2003/0164954 A1 | 9/2003 | Gerhard | |
| 2004/0032052 A1 | 2/2004 | Meyers et al. | |
| 2004/0143452 A1 | 7/2004 | Pattillo et al. | |
| 2004/0168329 A1 | 9/2004 | Ishimaru | |
| 2004/0181976 A1 | 9/2004 | Copesky et al. | |
| 2004/0250359 A1* | 12/2004 | Spivey | A61B 5/1078 12/142 N |
| 2004/0260508 A1 | 12/2004 | Pattillo et al. | |
| 2005/0030372 A1 | 2/2005 | Jung et al. | |
| 2005/0049816 A1 | 3/2005 | Oda et al. | |
| 2005/0203712 A1 | 9/2005 | Lowe | |
| 2006/0098896 A1 | 5/2006 | Pishdadian et al. | |
| 2007/0011173 A1 | 1/2007 | Agostino | |
| 2007/0253004 A1 | 11/2007 | Danenberg et al. | |
| 2008/0097720 A1 | 4/2008 | Tadin et al. | |
| 2009/0240514 A1 | 9/2009 | Oexman et al. | |
| 2013/0172787 A1 | 7/2013 | Marovets | |
| 2014/0033829 A1 | 2/2014 | Xia et al. | |
| 2014/0107967 A1 | 4/2014 | Xia et al. | |
| 2014/0107968 A1 | 4/2014 | Xia et al. | |
| 2014/0309534 A1* | 10/2014 | Pichler | A61B 5/1036 600/476 |

FOREIGN PATENT DOCUMENTS

| | | |
|---|---|---|
| EP | 0119660 A1 | 9/1984 |
| EP | 0173396 A2 | 3/1986 |
| EP | 0534503 B1 | 9/1997 |
| FR | 2776175 A1 | 9/1999 |
| GB | 2349728 A | 11/2000 |
| JP | 3251203 A | 11/1991 |
| JP | 7275307 A | 10/2007 |
| NL | 9100591 | 11/1992 |
| SU | 1814877 A1 | 3/1991 |
| TW | 200525400 A | 8/2005 |
| WO | 9723769 | 7/1997 |
| WO | 2008036397 A2 | 3/2008 |

OTHER PUBLICATIONS

Chu, Woei Chyn, et al., "The Use of Arch Index to Characterize Arch Height: A Digital Image Processing Approach" IEEE Transactions on Biomedical Engineering, Nov. 1995, pp. 1088-1093, vol. 42(11), IEEE Service Center, Piscataway, NJ USA.

McPoil, Thomas G., "Relationship Between Three Static Angles of the Rearfoot and the Pattern of Rearfoot Motion During Walking," Journal of Orthopedic & Sports Physical Therapy, Jun. 1996, pp. 370-375, vol. 23(6), Orthopaedic and Sports Physical Therapy Sections of the American Physical Therapy Association.

Menz, Hylton B., "Alternative Techniques for the Clinical Assessment of Foot Pronation," Journal of the American Podiatric Medical Association, Mar. 1998, pp. 119-129, vol. 88(3), American Podiatric Medical Association, Bethesda, Maryland USA.

Torburn, Leslie, et al., "Assessment of Rearfoot Motion: Passive Positioning, One-Legged Standing, Gait," Foot & Ankle International, Oct. 1998, pp. 688-693, vol. 19(10).

Urry, Stephen R. and Wearing, Scott C., "Arch indexes from ink footprints and pressure platforms are different" published in "The Foot", Jun. 2005, pp. 68-73, vol. 15(2).

Wrobel, James S., "Reliability and Validity of Current Physical Examination Techniques for the Foot and Ankle," Journal of the American Podiatric Medical Association, May 2008, pp. 197-206, vol. 98(3).

PCT Search Report for International Application No. PCT/US2007/020476 mailed Sep. 4, 2008, Tobias Görlach.

Davis, B.L., et al., "Decomposition of superimposed ground reaction forces into left and right force profiles", J. Biomechanics, (Apr. 1993) vol. 26, No. 4-5, pp. 593-597.

EP Search Report for EP11192771 (dated Feb. 10, 2012).
EP Search Report for EP11192772 (dated Feb. 10, 2012).
EP Search Report for EP10171065 (dated Aug. 27, 2010).
EP Search Report for EP11192770 (dated Feb. 10, 2012).
ROC (Taiwan) Search Report (Englilsh Translation) dated Mar. 19, 2014 for ROC (Taiwan) Patent Application No. 102123875; 1 page.
U.S. Appl. No. 11/524,745, filed Sep. 21, 2006.

(56) References Cited

OTHER PUBLICATIONS

U.S. Appl. No. 13/350,178, filed Jan. 13, 2012.

* cited by examiner

| | Band A (Foot Length < 244mm) | |
|---|---|---|
| | Low Weight | High Weight |
| Low Arch | Product 1 | Product 2 |
| Medium Arch | Product 3 | Product 4 |
| High Arch | Product 3 | Product 3 |
| | Medium Weight | 135 lbs |

| | Band B (244mm ≤ Foot Length < 255mm) | |
|---|---|---|
| | Low Weight | High Weight |
| Low Arch | Product 5 | Product 6 |
| Medium Arch | Product 7 | Product 8 |
| High Arch | Product 7 | Product 7 |
| | Medium Weight | 160 lbs |

| | Band C (255mm ≤ Foot Length < 270mm) | |
|---|---|---|
| | Low Weight | High Weight |
| Low Arch | Product 9 | Product 10 |
| Medium Arch | Product 11 | Product 12 |
| High Arch | Product 11 | Product 11 |
| | Medium Weight | 180 lbs |

| | Band D (Foot Length ≥ 270mm) | |
|---|---|---|
| | Low Weight | High Weight |
| Low Arch | N/A | Product 13 |
| Medium Arch | N/A | Product 14 |
| High Arch | N/A | Product 14 |
| | Medium Weight | 190 lbs |

| | | |
|---|---|---|
| | Low Arch | 0.257 < Arch Index |
| | Medium Arch | 0.173 < Arch Index ≤ 0.257 |
| | High Arch | Arch Index ≤ 0.173 |

FIG.8a

FOOTCARE PRODUCT DISPENSING KIOSK

This application is a continuation of, and claims priority to, U.S. application Ser. No. 13/350,178, filed Jan. 13, 2012, which is a divisional of, and claims priority to, U.S. application Ser. No. 11/524,745, filed Sep. 21, 2006, now granted as U.S. Pat. No. 8,117,922, the contents of which are incorporated herein by reference thereto.

BACKGROUND

Conventional footcare products, such as orthotics, foot cushions, heel cups, etc., are typically sold from conventional retail displays. Although packaging may provide some guidance, customers may have to guess which products are appropriate, e.g., the customers' size, foot characteristics, and other attributes. However, even if a customer were given the opportunity to try on a product, the customer may not know the best type of support or size of footcare product for their particular foot characteristics, e.g., the arch type of the customer's foot. This practice may result in the customer buying multiple products before the customer finally finds a product that meets the customer's needs.

Custom foot-care products may also be sold to provide a customer with the proper level of support. Custom footcare products that have adjustable support, still may not be of the proper size for a customer's shoes and may require significant time to determine the proper size. Some custom footcare products are made by moldable material. However, this requires time to measure the foot and then a period of time to make the orthotic. Because these orthotics are custom-made, they are typically more expensive than pre-manufactured orthotics. Also, creating a custom molded orthotic generally requires a trained professional that measures the customer and makes or orders the orthotic.

BRIEF DESCRIPTION OF THE DRAWINGS

FIG. 8a illustrates an example decision matrix, according to an example embodiment of the present invention.

DETAILED DESCRIPTION

Figure 1:
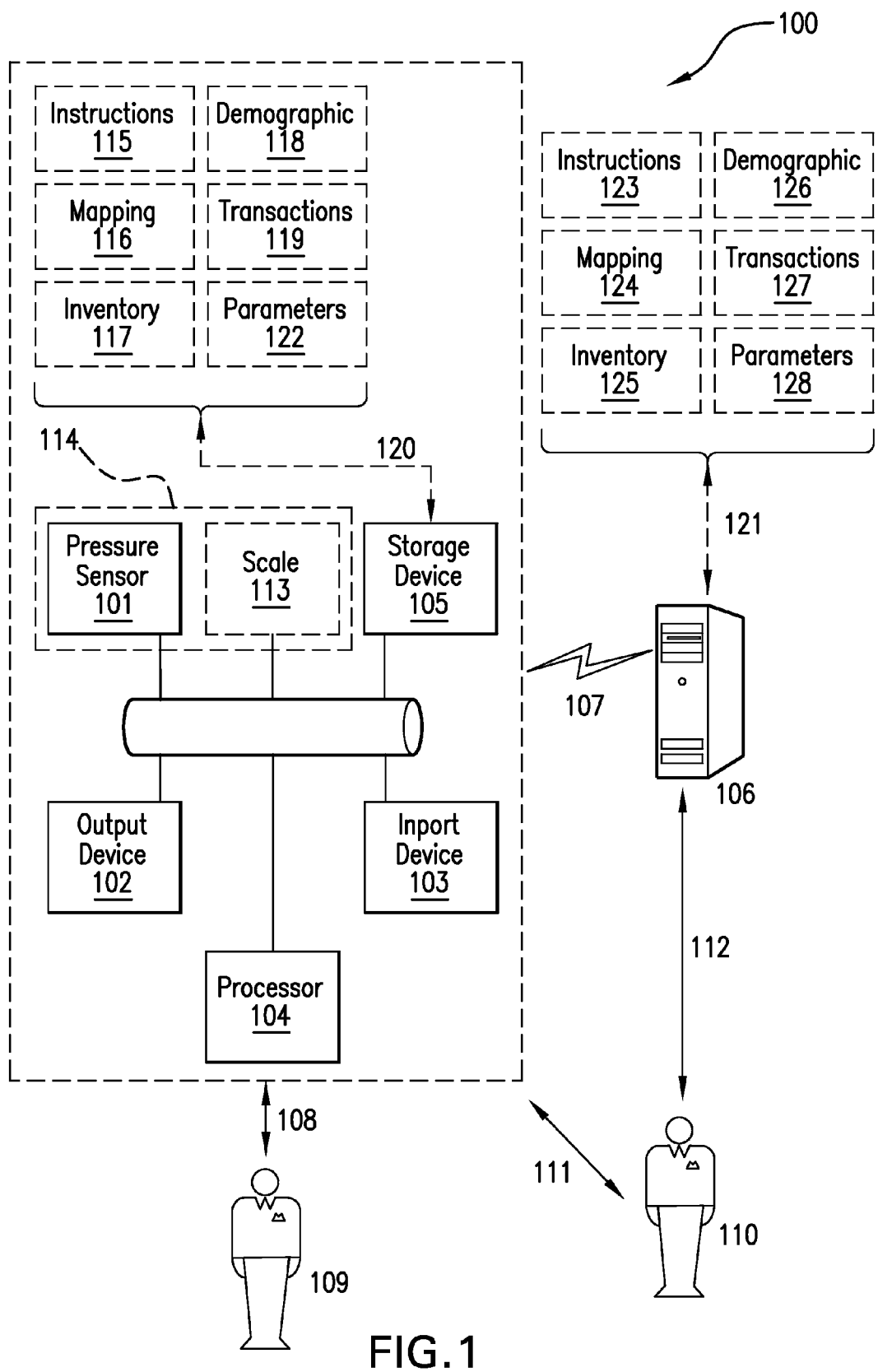
FIG. 1 illustrates a functional block diagram of an example kiosk, according to an example embodiment of the present invention.

Footcare products may be placed inside footwear products to provide support, cushioning, to improve fit or comfort, etc. Examples of footcare products include orthotics, insoles, foot cushions, heel cups, etc. Examples of footwear products include sneakers, loafers, dress shoes, high heels, etc. A person may want to quickly and accurately determine the proper footcare or footwear product for his or her feet from an available range or products. For example, a product may need to have the proper support, size, arch support, and be able to support the person's body weight. Retailers would also want to be able to provide this service to people without having to staff a person that has specialized training and/or knowledge of all possible products, footcare or footwear, and foot types.

In some example embodiments of the present invention, a kiosk measures a person's feet and determines a recommended footcare product for the person and the recommended product may be dispensed or may be selected by the person from a display. The measurements may be taken with a surface containing pressure sensors to measure a person's feet. A processor may correlate footcare products to the person's foot measurements. In one example embodiment, the kiosk may contain a video screen that provides instructions to the person. The system selects a recommended footcare product from among a set of candidate footcare products based at least in part upon a plurality of pressure measurements received from the pressure sensors. The set of candidate footcare products may be displayed on or near the kiosk in a merchandise display area, and the person would be provided with an indicia of the recommended footcare product, such as a picture of the footcare product, the model number of the footcare product, a color or symbol, etc. The person may then easily locate the footcare product that will provide the best calculated fit and support for the person's needs. Alternatively, products may be dispensed from a kiosk, for example, the kiosk may be configured as a vending machine. The footcare product sold may be a pre-manufactured orthotic, and the set of candidate footcare products may be a set of different models of pre-manufactured orthotics of varying attributes, such as size, arch support levels, arch index, cushioning levels (i.e. foam density, cushioning material used, etc.), etc. The range of models provided are chosen to address the most common conditions needing a footcare product, while coming in a range of sizes and models needed to fit and provide an appropriate support level for the vast majority of the potential user population.

One example embodiment of the present invention may be a system including a surface, wherein the surface is configured to allow a person to stand upon the surface; a plurality of pressure sensors located under the surface forming a 2-D array of sensors; a measurement system configured to obtain measurements from a customer's feet; a processor in communication with the plurality of pressure sensors, the processor configured to receive a plurality of pressure measurements from at least a subset of the plurality of pressure sensors while the person stands upon the surface, the processor further configured to select a recommended footcare product from among a set of candidate footcare products based at least in part upon the plurality of pressure measurements, wherein the processor is configured to receive at least a first subset of the plurality of pressure measurements while the person stands on one foot; an output device to display information received from the processor, the information identifying the recommended footcare product to the person; an input device configured to receive a person's input in selection of a recommended product; and a merchandise display area, the merchandise display area configured to display the set of candidate footcare products.

An alternative example embodiment of the present invention may be a method of selecting a recommended orthotic, including determining if a foot on a sensor is unshod; collecting a first set of pressure measurements of a foot of a person while the person stands stationary on one foot, wherein a plurality of pressure measurements are taken from different points of the foot of a person; calculating a biomechanical data estimate of the foot using the pressure measurements, wherein biomechanical data comprises foot length, foot width, body weight, arch index, outline of the foot and toeline, a peak pressure map, a longitudinal line drawn on a peak pressure map, or an intersection of a longitudinal line and a foot body; comparing the biomechanical data with values from a decision matrix of orthotics and classified subgroups; and selecting an orthotic based on the comparison.

An alternative example embodiment of the present invention may be an apparatus with a surface, multiple pressure sensors located under the surface, and a processor in communication with the plurality of pressure sensors, the processor configured to receive multiple pressure measurements from a subset of the multiple pressure sensors while the person stands upon the surface. The process may also be configured to select a recommended footcare product from among a set of candidate footcare products based at least in part upon the multiple pressure measurements. The surface may be configured to allow a person to stand upon the surface. Footcare products may include orthotics. The set of candidate footcare products includes a set of orthotics, the set including pre-manufactured orthotics with a plurality of different sizes and a plurality of different support levels. The pressure sensors may be a grid of pressure sensors, possibly formed of a 2-D array. There may be 1144 sensors in an array for a single foot. The sensors may be 7.5 mm×7.5 mm or smaller. The pressure sensors may include a pressure-sensitive conductive ink, a piezoelectric sensor, etc. The apparatus may select a recommended footcare product and the selection may be made without other foot measurements being taken other than the pressure measurements, in alternative embodiments, a scale may be used to provide a weight measurement of the person.

The example embodiment of the apparatus may also contain input and output features. The apparatus may contain an output device to display information received from the processor, the information identifying the recommended footcare product to the person. The output device may be a video screen configured to display an image of the recommended footcare product, a biomechanical data estimate, or display instructions, the instructions directing the person to stand on one foot. Biomechanical data may include at least one of the foot length, foot width, body weight, arch index, outline of the foot and toeline, a peak pressure map, a longitudinal line drawn on a peak pressure map, or an intersection of a longitudinal line and a foot body. The video screen may also be a touch screen, configurable to receive both input and output. A separate input device may also receive input to configure the processor.

The apparatus may also be configured to receive and calculate pressure measurements with a processor. The processor may be configured to take pressure measurements while the person stands on one foot or may be configured to receive at least a first subset of the plurality of pressure measurements while the person stands on one foot. The processor may be configured to receive at least a second subset of the plurality pressure measurements while the person stands on both feet. The processor may be configured receive demographic information.

To select a recommended footcare product, a storage device may store a mapping of footcare products to classified subgroups. The storage device may also store a storage record containing an apparatus transaction. The processor may be configured to calculate biomechanical data estimates based on the plurality of pressure measurements. The categories of biomechanical data estimates include estimated foot dimensions, estimated foot type, and estimated body weight. Foot dimensions may be a longitudinal line that runs from the center of a heel to the center of a second toe, a toe line that is a fitted curve through three alignment marks, a foot length that is the projection of the distance between the most anterior point and most posterior point of foot pressure map on the longitudinal line, a foot width that is the projection of distance between the most medial point and most lateral point of foot pressure map on the perpendicular line of the longitudinal line, the arch index that is the ratio of the area of the middle third of the toeless footprint to the toeless footprint area, etc. The processor may be configured to select a recommended footcare product based on the biomechanical data estimates. The processor of the apparatus may also be configured to determine whether an unshod foot, a shoe, or a sock is on the pressure sensors. The processor may use some of the biomechanical data estimates or pressure measurements to make this determination.

As stated above, the apparatus may select a recommended footcare product from a set of candidate footcare products. The set of candidate footcare products may include a set of different pre-manufactured orthotics. The set of different pre-manufactured orthotics may include orthotics that differ in size, arch support levels, and cushioning levels. The set of different pre-manufactured orthotics variations may be calculated to fit the majority of the population. The processor may be configured to receive accuracy factors from a person. The accuracy factors may be received before making the recommendation or after making a recommendation. The accuracy factors may be integrated with the calculations and procedures performed for selection of the recommended footcare product but may also be a complete separate procedure. The apparatus may also include a merchandise display area configured to display the set of candidate footcare products.

An example embodiment of the present invention may be a point-of-sale system for selling orthotics including a set of pre-manufactured orthotics of different types, a measurement system configured to obtain measurements from a customer's feet, and a processor configured to receive the measurements and to recommend an orthotic to the customer from the set of pre-manufactured orthotics based at least in part on the measurements. The measurement system may contain a plurality of pressure sensors. The processor may be configured to derive biomechanical data from measurements collected by the measurement system. The biomechanical data may be selected from the foot length, foot width, body weight, arch index, outline of the foot and toeline, a peak pressure map, a longitudinal line drawn on a peak pressure map, and an intersection of a longitudinal line and a foot body, among others. A dispensing mechanism may provide an orthotic from the set of pre-manufactured orthotics to the person.

An example embodiment of the present invention may also perform a method of characterizing a foot. The method may collect a first set of pressure measurements of a foot of a person while the person stands stationary on one foot and characterize the foot based on the first set of pressure measurements. Selection of a footcare product may then be based on the characterization of at least the one foot. The method may collect a second set of pressure measurements from both feet of a person while the person stands on both feet and characterize the foot based on the first set and second set of pressure measurements. Alternatively, the method may only collect pressure measurements from both feet as the first set of pressure measurement of a person and characterize the foot based on the first set, in this example, the pressure measurements of both feet. The method may also calculate a biomechanical data estimate of the foot using the pressure measurements. The method may compare the biomechanical data with values from a decision matrix of orthotics and classified subgroups, wherein a classified subgroup may include the weight of the person, the band of the person (i.e. a band based on a person's foot length), a person's arch index, etc. The method may involve calibrating a plurality of pressure sensors and a processor using a Force Calibration method or a Multi-level Pressure Calibration method. The method may involve adjusting coefficients in a processor change the accuracy factors to recommend an orthotic. The decision matrix may be created based on a product specification list.

An example embodiment of the present invention may also perform a method of selecting an orthotic. The method may include collecting a plurality of pressure measurements at different points of the foot of a person and selecting an orthotic based on the pressure measurements. The method may perform a combination of grouping a person into one of a plurality of classified subgroups based on the pressure measurements; recommending a footcare product based on a person's classified subgroup; deriving biomechanical data estimates from the pressure measurements of at least one of the both feet of a person, the left foot of a person, or the right foot of a person; estimating the biomechanical data of the person's feet using the first set of pressure measurements and the second set of pressure measurements; confirming the person is balanced based on the received pressure measurements; confirming the person is not wearing a footwear based on the pressure measurements; confirming the person is not wearing a footwear based on the biomechanical data estimates; receiving the second set of pressure measurements when the load on the individual planting foot reaches a pre-determined bodyweight percentage; receiving the second set of pressure measurements when the person's Center of Force enters a target zone, wherein a target zone is a pressure reference point; receiving the second set of pressure measurements when the Center of Force matches a target zone and at least 95% of static weight, weight calculated by the sum of forces created by the feet when relatively still, is achieved; or generating a static foot outline based on pressure measurements. Biomechanical data may include foot length, foot width, body weight, arch index, outline of the foot and toeline, a peak pressure map, a longitudinal line drawn on a peak pressure map, or an intersection of a longitudinal line and a foot body. A specified bodyweight percentage may be between the range of 90 to 95 percent of bodyweight.

An example embodiment of the present invention may also perform a method of determining if a foot on a sensor is unshod. The method may include determining plurality of foot dimensions, calculating a plurality of foot dimension ratios, and comparing the foot dimension ratios to predetermined values (e.g. 3.5, 6.0, 1.2, and 0.1). The foot dimensions may be selected from the group consisting of foot length, heel width, arch width, and forefoot width, although it will be appreciated that other dimensions may also be used. Foot dimension ratios may include foot length (e.g. the length of the line between the most posterior and most anterior points of each foot pressure print) over the heel width (e.g. the length of a first line that is perpendicular to a second line, wherein the second line is a line between the center of the heel and the center of the second toe, and the first line is located at 16%, though it may range between 5 to 20%), forefoot width/heel width, and arch width/heel width.

FIG. 1 illustrates a functional block diagram of an example kiosk, according to an example embodiment of the present invention. The example kiosk 100 may be used to take a person's foot measurements, and based on the measurements, select a recommended footcare product. The kiosk 100 may include a foot measurement subsystem 114, e.g., a plurality of pressure sensors 101. The pressure sensors 101 may be provided by using a pad having an array of pressure sensors made from pressure sensitive conductive inks, e.g., sensors from Tekscan, Inc. (307 West First Street, South Boston, Mass. 02127-1309, USA), and/or sensors described in U.S. Pat. Nos. 5,989,700 and 6,964,205. Other measurement technologies may also be employed. e.g., force plates, piezoelectric sensors, digital air pressure sensors, optical measurements, gauges, thermal sensors, etc.

The pressure sensors 101 may be arranged to obtain pressure measurements at different points of a person's foot. For example, the pressure sensors may be arranged as a 2-D grid or a 3-D grid of multiple sensor layers. Sensels of up to 7.5 mm by 7.5 mm arranged in an array provide adequate detail to characterize feet up to men's size 15. The sensing element may provide the measurements needed to provide an accurate pressure map of the foot. For example, in one example embodiment, given the square footage of the pressure pad, a minimum of 1144 number of pressuresensors per foot area with a size of 6.86 mm×6.65 mm provides an accurate pressure map of a foot. Thus, for two feet there would be 2288 pressure sensors. However, with a varying range of sensor sizes, the number of sensors that may be needed to accurately capture a pressure map of the foot may vary. The foot area, and correspondingly the number sensors, may also vary depending on the target population. For example, an example embodiment of the kiosk may contain pressure pads underlying the feet that are capable of measuring children to adults, and the pads underlying would be large enough to capture the foot area of an adult.

The pressure measurements taken from the plurality of pressure sensors 101 may, but need not, be the only measurements of the foot collected to select a recommended footcare product. For example, in alternative embodiments, a scale 113 may also be employed in the foot measurement subsystem 101 to provide greater accuracy in estimating a person's weight. It will be appreciated that measurement approaches that produce a relative pressure distribution, without producing absolute pressure values, may also be employed in place of absolute numerical pressure measurements.

The example kiosk 100 may also contain an output device 102, such as a video screen or LCD screen, and an input device 103, such as a keyboard, mouse, etc. An alternative embodiment may contain a touch-screen as a combination of the input device 103 and the output device 102. The output device 102 may display information received from a processor 104. Such information may include a recommended footcare product in the form of a picture or a model number, instructions on how to use the kiosk, biomechanical data estimates, data containing kiosk transaction information, etc. The output device 102 may display foot pressure in real-time as soon as a user steps onto the pressure sensors. If the output device is a digital display, the pressure may be displayed in pixel format or contoured format, i.e. a real-time smoothed version of the pixilated format for aesthetic display purposes. The display may also show in real-time a pressure map and changes in the pressure map of a person's feet while the person stands on the pressure sensors.

The output device 102 may also display a final peak pressure map to a person. The peak pressure map is the combination of the peak at each specific point. A dynamic pressure display may use a fixed color legend while a peak pressure generated after data collection may use a floating (variable) legend based on the range of peak pressure. The various pressure maps, such as the peak pressure map, may be used by other embodiments of a kiosk to detect hot spots and recommend therapeutic products or pads. For example, hot spots may be used to detect where the peak pressure is applied in various areas of the foot. Pads or other cushioning foot products may then be recommended to apply to those areas.

While a person, such as a customer 109, may use the input device 103 to perform a procedure 108 to select a recommended footcare product based on the pressure measurements of a person's foot, another person, such as an administrator 110, may use the input device 103 to configure 111 the processor 104. Configuring 111 may involve adjusting the parameters used to select a recommended footcare product, calibrating the pressure sensors, providing new product listings, etc.

An administrator 110 may calibrate the processor 104 to ensure the accuracy of the pressure measurements taken from the pressure sensors 101. Two methods may be employed by an administrator 110: a Force Calibration (FC) or a Multi-Level Pressure Calibration (MPG). Using a Force Calibration method, an administrator 110 measures a tester's body weight on a calibrated weight scale and subsequently measures the tester's body standing on the pressure mat 114. The body weight of the tester is entered into the processor and the tester would stand still on the pressure mat for a fixed duration before starting the calibration process. The fixed duration may range from as low as 1 second to 15 seconds. A system that could collect data or frames at higher rates could decrease the time needed.

Using a Multi-level Pressure Calibration method, an automatic sensitivity adjustment may be executed. In the calibration window, a "sensitivity setting" button may be added. A tester may insert the pressure mat in the calibration mat in the calibration device and load the pressure mat at a fixed known pressure, such as 15 pounds per square inch (psi). The process may involve adjusting sensitivity based on raw digital readings. To conduct the multi-level pressure calibration, the entire pressure platform may be placed in a pressure calibration device. The pressure mat may then be loaded at various pressure levels, such as 5 psi, 10 psi, 15 psi, 20 psi, 30 psi, etc. A load-output curve is generated for each sensel on the pressure mat, the sensel being an independent sensing cell. Moreover, in order to ensure proper calibration, the processor may perform a test calibration of the pressure sensors in order to offset long-term drifting.

The example kiosk 100 may also contain a storage device 105, e.g. RAM, a hard drive, flash drive, etc. that may transfer 120 information to be stored or sent, such as the instructions or software upgrades 115 needed to operate the kiosk, a mapping or decision matrix 116 of footcare products to classified subgroups, an inventory list 117, demographic information 118 of people that use the kiosk, parameters 122 of the kiosk that are pre-configured and which may be set by an administrator, records of kiosk transactions 119, demographic information 118 relating types of footcare products selected for foot types, etc. The inventory list 117 may store information of the types of products and also current availability in stock of those products. This information may also be transferred across a communication medium 107, e.g. a modem, DSL, cable, ethernet, etc., to network servers 106 which may transfer 121 the stored kiosk information from a plurality of kiosks 100.

The network servers 106 or databases may store the corresponding information from a plurality of kiosks 100, including instructions or software upgrades 123, mappings or decision matrices 124, inventory 125 or product lists, demographic information 126, transactional information 127, and parameters 128. It may appreciated that the operation of the networked kiosks may alternatively be controlled through instructions or software upgrades 123 located only on the network servers 106. Alternatively, networked kiosks may share instructions and operational control with the server 106. An administrator 110, may collect and analyze 112 data from the network servers 106 to adjust parameters used to select a recommended footcare product or to adjust shipment of certain models of footcare products. Moreover, the inventory 125 may be analyzed, as will be explained later, to track the sales statistics of inventory or to register whether certain kiosks need to be restocked or more products need to be manufactured.

A processor 104 in the example kiosk 100 may be configured to perform a variety of tasks, such as taking pressure measurements from the pressure sensors 101. The processor may be able to calculate biomechanical data estimates of a person's foot based on the pressure measurements. Biomechanical data estimates may include estimated foot dimensions, estimated foot type, and estimated body weight. Foot types may indicate whether the person has flat feet, supination, pronation, etc.

At the end of kiosk use, or before it is used during the day, an administrator 110 may initiate a checkup, or alternatively, the kiosk may initiate a self-check-up. A self-check-up may involve a pressure mat condition check-up (sensel misfiring when there is no load), handle-sensor, handle-computer check-up, touch screen check-up, system memory clean-up, calibrating the pressure mat, calibrating a scale, accounting for daylight savings time, etc.

Prior to the start of the kiosk, or while the kiosk is not in use, an administrator 110 may access the processor 104 using the input device 103 or the output device 102 that can act as an input, such as a touch screen interface. Or, if there is an error while the kiosk is in use, the error may prompt administrator 110 action. An administrator may set parameters for error-checking, such as a weight range limit, equation coefficients to calculate biomechanical data estimates or to select a footcare product. An administrator may also download from a network 107 or upload into the storage device 105 new product lists, inventory 117, video clips, language templates, etc.

Figure 2:
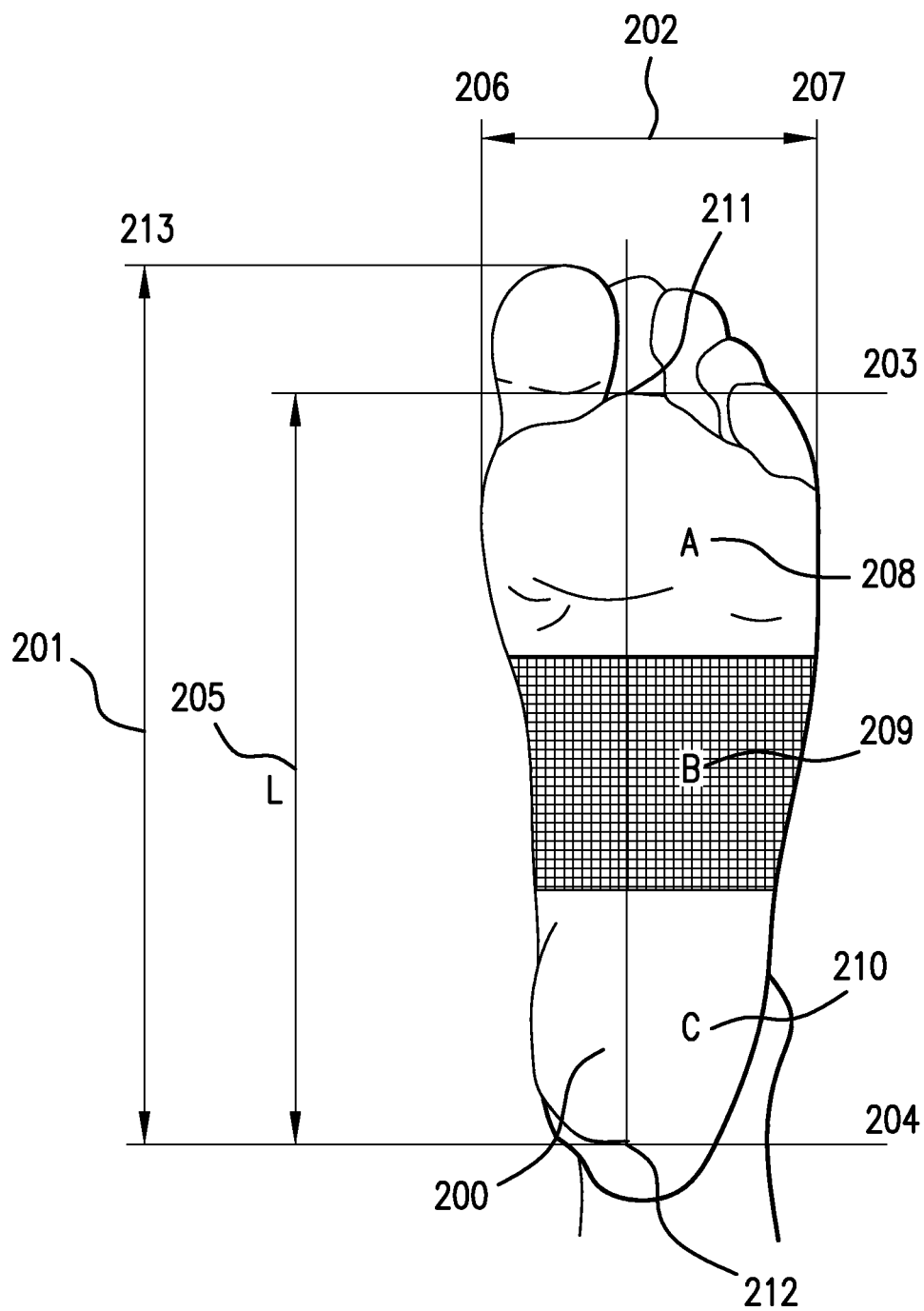
FIG. 2 illustrates several example foot dimensions.

FIG. 2 illustrates several example foot dimensions. The example estimated foot dimensions may be calculated based on pressure measurements taken by the example kiosk described previously. A foot dimension may be a longitudinal line 200 that runs from the lateral center of a heel to the lateral center of a second toe. Foot length 201 may be the distance between the most posterior point, i.e. the point towards the heel, of the foot 204 and the most anterior point 213, i.e. the point farthest toward the toes, on the foot pressure map on the longitudinal line. Foot width 202 may be the projection of distance between the most medial point 206 and most lateral point 207 of the foot pressure map, the projected foot width shown in the figure being perpendicular to the longitudinal line 200. An arch index is an estimate which may be used to characterize the arch. An arch index may be defined as the ratio of the area of the middle third of the toeless footprint to the total toeless footprint area, known as the foot body. The division of the three segments is along a line L 205 that is drawn between the lateral center point of the second toe 211 at the level of the toe line 203 and the lateral center of the heel 212 on the level of the most posterior point of the heel 204. The foot is thus divided into thirds, A 208, B 209, and C 210, with each third being of length L divided by 3. The Arch Index is equal to the areas of B/(A+B+C), which is equal to the area of B divided by the Foot Body Area. It may be appreciated that foot dimensions may be estimated using alternative methods or based on alternative points of measurement.

Figure 3A:
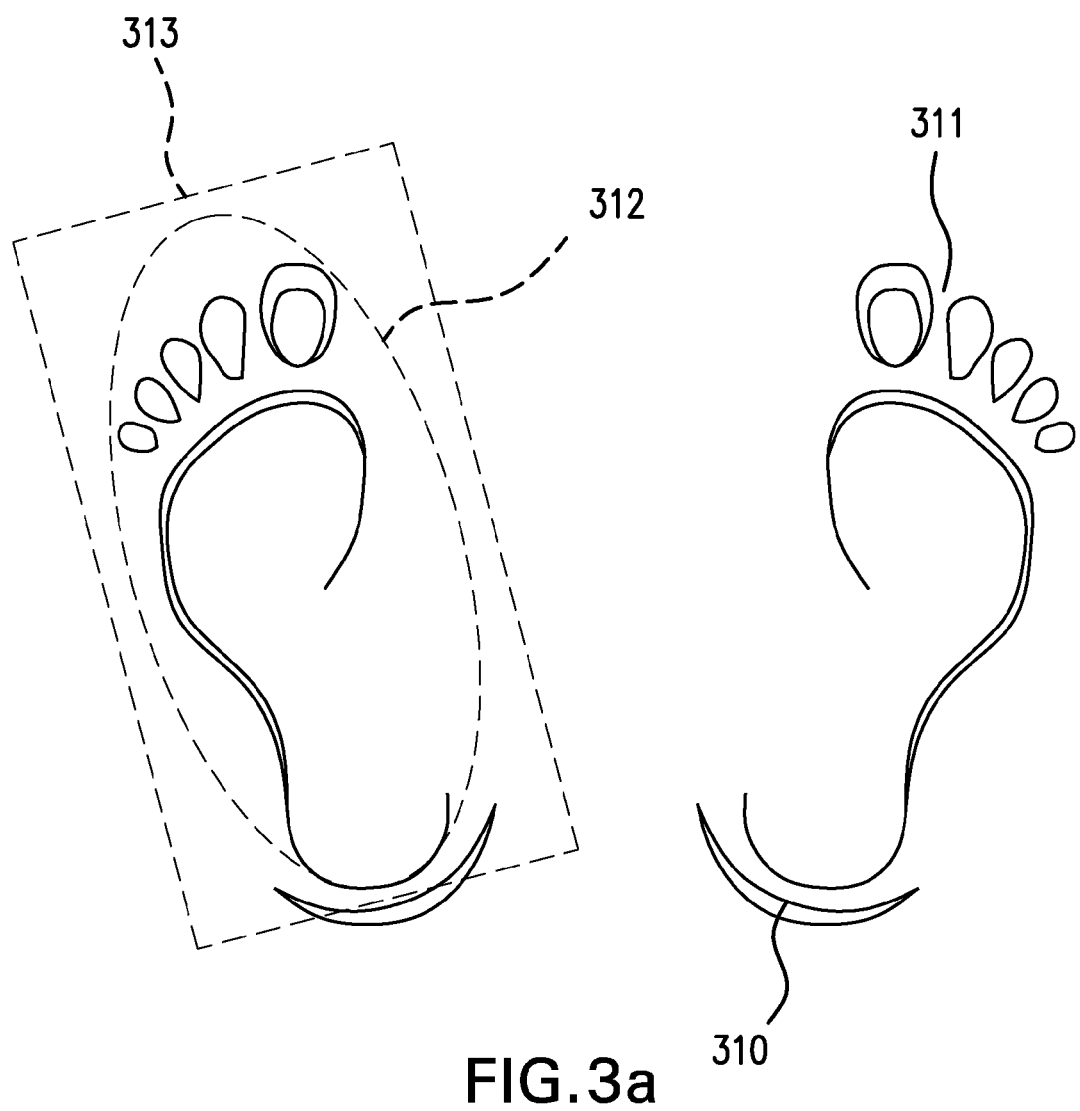
FIG. 3a illustrates an example of the locations of alignment marks that may be displayed on a pressure mat.

FIG. 3a illustrates an example of the locations of alignment marks that are displayed on a pressure mat. When a person stands on a pressure mat his feet should be located at the approximate angle of the two feet-shaped outlines 311. An alignment border 310 marks the furthest posterior boundary capable of receiving measurements. Internally the sensor array grid may detect features of the foot. As long as some part of the region of measurement can be taken it can be determined whether a person being measured is standing outside the measurement grid. The person would them be instructed in how to move his feet in order to be within the measurement area. For example, one way of determining whether a foot is in a measurement region is to determine whether a part of a foot is on one side of the measurement grid, e.g., whether measurements can be taken on the sensor grid outside the measurement grid. Thus, a measurement grid 312 may be defined within a larger actual sensor grid 313 array boundary. It sensors detected measurements within 312 and also within 313 near that same area, then the system would recognize that a foot was outside the boundary and direct the person to adjust his foot.

Figure 3B:
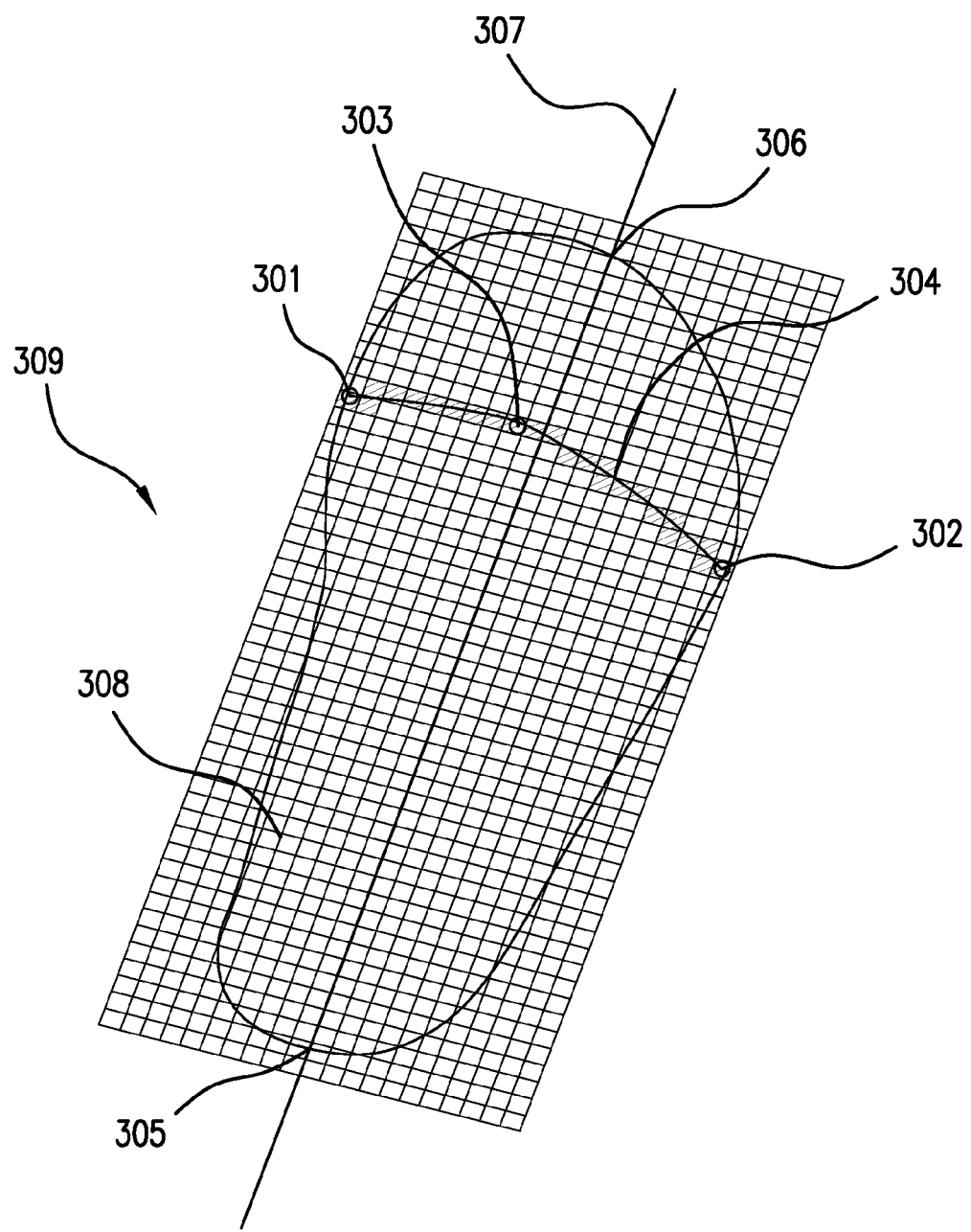
FIG. 3b illustrates measurements that may be derived from pressure measurements on a pressure mat.

FIG. 3b illustrates measurements that may be derived from pressure measurements on a pressure mat. In this alternative method of determining alignment, a person may stand within a designated area like in FIG. 3a. A longitudinal line 307 may be calculated to provide prospective of the location of a line connecting the center of the heel 305 and the center of the second toe 306. The outline 308 of the foot may be the general measurable boundaries for a person to place his or her foot. The outline may be large enough to fit a majority of people. For example, in one embodiment, a little more than 6 inches may be provided for toes. A grid 309 may be provided in order to provide uniform measurement units and they may, but need not, be provided to the person standing on the pressure mat.

Three Alignment Marks, X 301, Y 302, and Z 303 are designated across the width of the outline 308. Alignment Mark X 301 may be derived by taking the 100% multiplied by the ratio of the Average First Metatarsal Length over the Average First Toe Length. Average lengths may be derived by studying the mean foot lengths tailored to groups of people based on race, gender, foot type, or an overall population. Alignment Mark Z 303 may be derived by taking 100% multiplied by the ratio of the Average Fifth Metatarsal Length over the Average Fifth Toe Length minus a predefined number of grids. Alignment Mark Y 302 may be derived by taking an average length differential between the second and first metatarsal heads in the longitudinal direction. A generally hyperbolic fitted curve may be drawn over the three points to represent a toe line 304. It may be appreciated that the average lengths may have some variation, and thus, the exact location of the Alignment Marks may deviate slightly.

In one embodiment, Alignment Mark X 301 may be estimated to be 73% of the pressure mat length (=100%*19.29/26.32=38 grids; 19.29=average Canadian first metatarsal length; 26.32=average Canadian first toe length). Alignment Mark Z 303 may be estimated to be 64% of the pressure mat length 100%*16.9/21.69; 16.9=average Canadian fifth metatarsal length; 21.69=average Canadian fifth toe length). Each grid may be equal to 673 mm. One average length differential between the second and first metatarsal heads in the longitudinal direction is 3.4 mm while another average is 3.2 mm. Taking the average of the two averages would derive an average of 3.35 mm. Assuming an average foot length of 26.32 cm, the location of the second metatarsal head location may be moved up by 4.45 mm (=3.35*35/26.32). If each grid is equal to 6.73 mm, the location of Alignment Mark Y 302 may be moved approximately ⅔ of the distance of a single grid. The location of center of the heel 305 and the center of the second toe 306 may be derived from averages, but in this example embodiment, it is defined to be between the ninth and tenth grid in the lateral direction.

Figure 4:
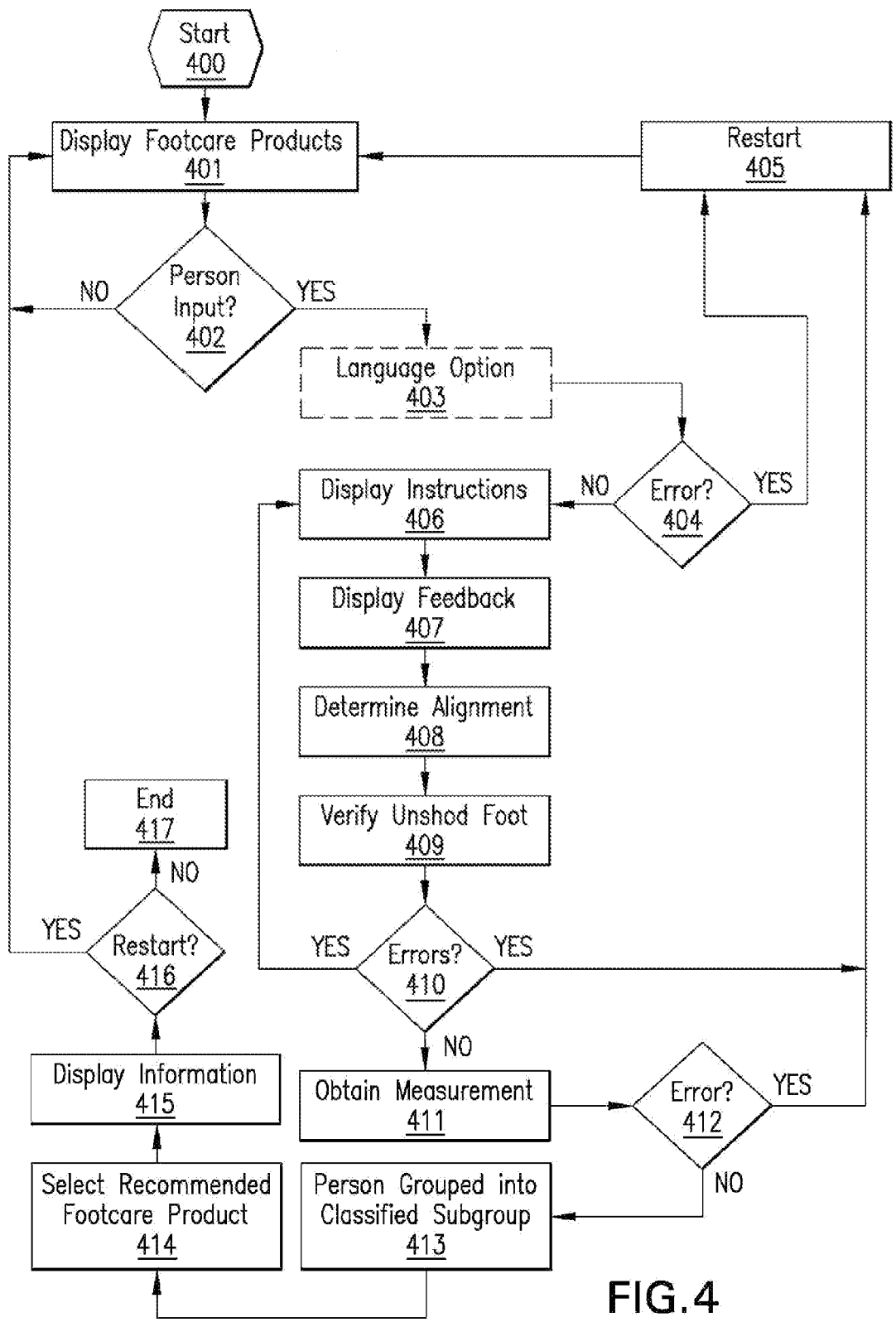
FIG. 4 illustrates a flowchart of an example procedure for characterizing a person's feet based on pressure measurements and selecting a recommended footcare product, according to an example embodiment of the present invention.

FIG. 4 illustrates a flowchart of an example procedure for characterizing a person's feet based on pressure measurements and selecting a recommended footcare product, according to an example embodiment of the present invention. The example procedure may be implemented by a kiosk, such as the example kiosk described in FIG. 1. In 400, the example procedure may be initiated by an administrator. In 401, an output device may display an attract screen, e.g., pictures of products that may be sold in a merchandise display area of an example kiosk, and awaits a person's input 402. While there is no input, the attract screen may continue to display footcare products 401 or other images to attract a person. In an alternative embodiment, a dispensing mechanism may replace a merchandise display area, and the dispensing mechanism may automatically, or at the request of the person, begin the procedure to dispense the recommended footcare product. Intermittent audio and video clips may accompany the display of the footcare products.

When a person responds to the attract screen, e.g. by touching a touch screen or pressing a start button, the procedure may indicate that various language options 403 may be available, e.g., English or Spanish. The person may indicate a language preference and an error-check may be performed 404. While pressure measurements are taken, while a person's feet is grouped into a classified subgroup, or while a recommended footcare product is being selected, various screens may be displayed. At each of these screens, errors may occur or the user may voluntarily abort the procedure. These errors or aborts and the corresponding screen that it occurred may be tracked, e.g. by storing in the kiosk storage device or sending over a network to be tracked at a server 106. If an error or abort occurs, the procedure may restart 405 and return to its waiting mode by displaying footcare products 401.

If an error did not occur in 403, at 406, the procedure may re-display the instructions or display more detailed instructions. The person may place his feet on the pressure mat, if the person had not done so already. In 407, the display may provide a person with feedback, e.g., showing a real-time display of a pressure map of the person's feet. In 408, a person may be instructed to align the person's feet, for example using with alignment marks such as those in FIG. 3b. Alignment marks may be displayed that match the exact pressure map locations. Alignment marks may include toelines and longitudinal lines for the left and right foot and may be illustrated by different zones of color. The center of the heel and the center of the second toe may automatically be detected. If it is not, a longitudinal line may be displayed and a person may be asked to adjust the foot until the feet are aligned with the longitudinal line. Alternatively, as in FIG. 3a, the user may be prompted to move his feet within the boundaries as detected by pressure sensors. The kiosk may determine if the feet are out of bounds of the pressure mat, whether the person's body weight is out of a predetermined range, or whether a person's feet are unshod. In 409, whether a person has unshod feet while standing on the pressure mat may be verified.

In 410, multiple error checks may be performed. Based on prior determinations, errors are flagged if the issues may not be resolved. These errors may include: (1) if it cannot be recognized that a person is standing on the pressure with unshod feet (even if the person is); (2) if the person is standing out of the bounds of the pressure mat; (3) if the person has their feet misaligned; or (4) if the person's weight is not placed evenly on the pressure mat. Moreover, other error checks may be determined. For example, a minimum and maximum limit for a person's weight may be determined. It may be required that a person weigh between 70 and 400 pounds. It may be appreciated that a weight range may vary and also be represented in other metrics. As a result of the errors, the procedure may attempt to re-display the instructions 406 in order to help the person resolve any issues. The procedure may reach a threshold where the issues may not be easily resolved and thus restart the entire procedure 405.

If there are no errors, the procedure continues to 411. In 411, measurements of the feet may be obtained, e.g. pressure measurements from an array of pressure sensors. Throughout the measuring process, the person being measured may abort the procedure, e.g., by stepping off the pressure mat. The procedure may be also be aborted if there are problems in the measurement process, such as by the user shifting his weight unevenly. In 412, any measuring errors or aborts may be detected. If the issue cannot be resolved, the procedure may be re-started 405. In 413, based on the pressure measurements and biomechanical data estimates, a person may be grouped into a classified subgroup. In 414, a recommended footcare product is selected for the person based on a decision matrix or a mapping. For example, a product may be selected for a person based on physical characteristics such as arch index, weight, or foot length.

In one embodiment, the footcare product may be a pre-manufactured orthotic. In alternative embodiments, the processor or pressure sensors may be configured to collect pressure measurements to select another footcare product, e.g. a heel cup, a pressure pad, etc. The same pressure measurements may be implemented in the selection and recommendation procedures for different types of footcare products. However, alternative points may be taken from a pressure mat to recommend different types of footcare products. For example, while the same pressure measurements may be used to recommend an orthotic and a heel cup, alternative points of measurements concentrated in the heel may be more accurate to determine a heel cup fit. Both methods may be used and the processor and pressure sensors need only be configured to accommodate both footcare products.

Alternatively, in 414, multiple footcare products may be selected for a person to choose from. The person may also be prompted to answer questions providing additional information, for example, in order to provide the procedure with accuracy factors that can adjust parameters to search for a more accurate match. Such accuracy factors may use preferences, types of activities that the person frequently engages in, the type of shoes that the footcare product may be used with, gender of the person, etc. in order to further narrow the list of selected orthotics. Alternative questions may be asked earlier in the procedure, such as before the pressure measurements are taken. Alternative factors may change the recommended footcare product from one type of footcare product to another, e.g. an orthotic versus a heel cup.

In 415, several types of information may be displayed, e.g. to the person using the kiosk described above. Indicia identifying the model of the recommended footcare product may be displayed. These indicia may help the person locate a corresponding footcare product that is located in a merchandise display area. Moreover, along with the real-time pressure measurements that a person may already view, a peak pressure map may be displayed to show the pressure measurements taken by the kiosk. Information regarding any of the biomechanical data estimates, such as estimated weight, foot type, or others may also be displayed. Examples of biomechanical data estimates that may be displayed include foot length, foot width, body weight, arch index, outline of the foot and toeline, a longitudinal line (drawn on the peak pressure map), or the intersection of the longitudinal line and foot body, i.e. the area of the foot excluding the toes.

In 416, after the person has completed the measurements and received information about the recommended footcare product, the person can choose to restart the process or the person can step off the measuring device, which would automatically restart the procedure to display foot care products, in 401, while waiting for a new person to initiate the procedure.

If a person were to use the procedure with the example kiosk of FIG. 1, values may be stored or sent over a network regarding kiosk transactions that were performed. Examples of kiosk transaction information that may be stored are the number of times the kiosk has been used, the number of times the system was used to completion of selecting a footcare product to a person, if a person aborted use of the kiosk and at which screen the person was viewing at the time of aborting, a count of which products have been recommended, and a total count of persons that used the kiosk and the time of day that the kiosk was used as well as the length of time spent using the kiosk per person. If the kiosk is not activated for a significant period or if the kiosk is scheduled to operate during only certain times of the day, the last person may be measured and the kiosk may automatically shutdown or go to sleep in 417.

Figure 5:
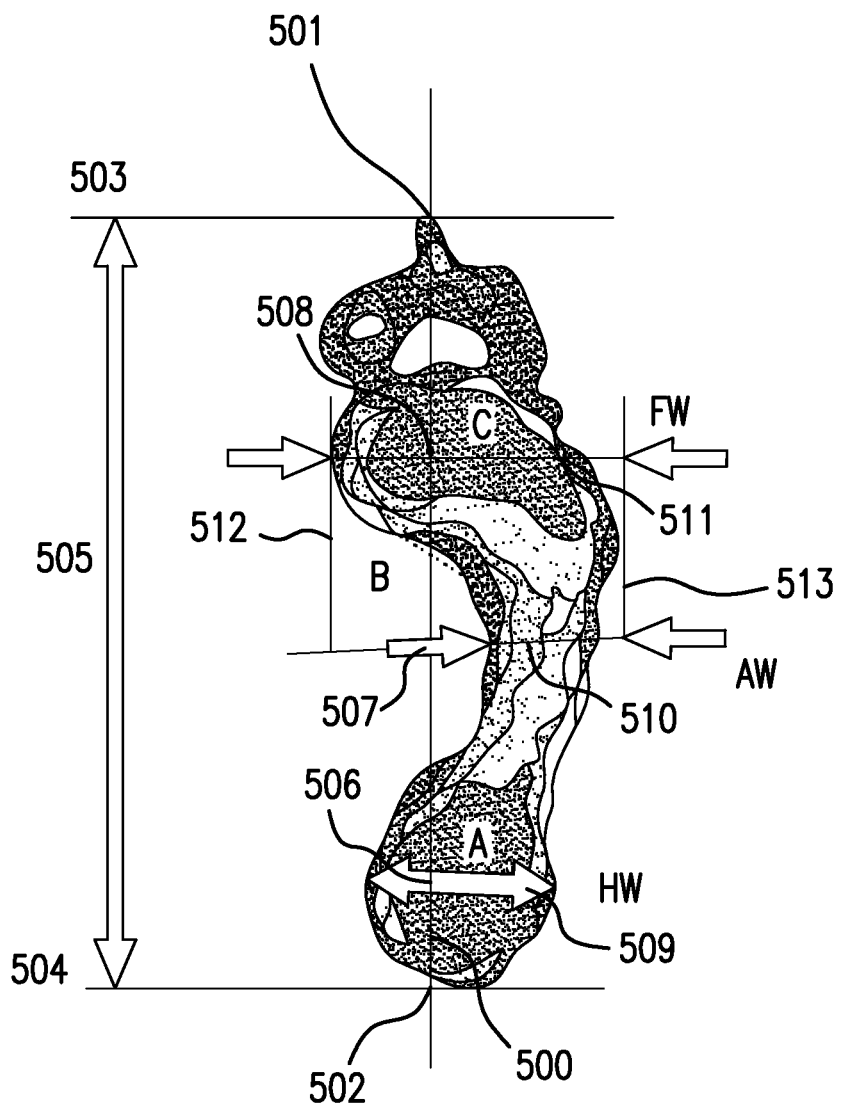
FIG. 5 illustrates an example pressure map showing foot dimensions that may be used to determine if a foot on a sensor is unshod, according to an example embodiment of the present invention.

Measurements of a person's foot vary significantly if the foot is not unshod. Accordingly procedures may be provided to automatically detect whether a footwear is worn by a person whose foot is being measured. FIG. 5 illustrates an example pressure map showing foot dimensions that may be used to determine if a foot on a sensor is unshod, according to an example embodiment of the present invention. The pressure map may be generated after collecting a static pressure for a prescribed period of time, for example, 2 seconds. On the pressure map, a longitudinal line 500 connects the lateral center of the heel 502 and the lateral center of the second toe 501. The center of the heel and the center of the second toe (and any other point of interest) may be determined by comparing the measured foot profile with general foot templates. Generalized foot templates may be created by taking samples of actual feet measurements or averaging many foot types. Based on the pressure map, a geometric center of the feet may be determined. The general foot templates may expand or shrink depending on the size or length of the foot and the general foot template may be compared to that of the pressure map outline using the geometric center as a reference point. A matching method, such as best fit, may then be used to determine the most comparable general foot template. Using the most comparable general foot template, all other points of the foot may be estimated, including the center of the heel and center of the second toe.

For the purpose of clarity and explanation, in FIG. 5, the most anterior point and the most posterior point along the longitudinal line are projected out as the most posterior point line 503 and the most anterior point line 504, which are perpendicular to the longitudinal line. The projection of the line between the most posterior point and most anterior point is the Foot Length (FL) line 505, which is equal to the distance between the most posterior point and the most anterior point. Three points are identified along the longitudinal line measured in relation to the foot length. These are point A 506, measured at 16% of the FL line 505 from the posterior end, point B 507, measured at 50% of the FL line 505 from the posterior end, and point C 508, measured at 75% of the FL line from the posterior end. It may be appreciated that these points may vary, and these points may derived from trial runs on the feet of approximately 30 test subjects.

Line A 509, is perpendicular to the longitudinal line and is drawn through point A 506. Line A 509 intersects with the boundaries of the pressure map, and the length of Line A 509 may be truncated within the outline of the pressure map. The outline of the pressure map indicates the outermost pressure points that are reflected in a real-time pressure measurement. The length of Line A 509 represents the Heel Width (NW). Line B 510, is perpendicular to the longitudinal line and is drawn through point B 507. Line B 510 intersects with the boundaries of the pressure map in the midfoot area and the length is truncated within the outline of the pressure map. The length of Line B 510 represents an estimate of the Arch Width (AW). Line C 511, is perpendicular to the longitudinal line and is drawn through point C 508. The widest points between Line B 510 and Line C 511 are projected out as lines, parallel to the foot, on the medial side 512 and the lateral side 513. The longest width of the pressure map between. Line B 510 and Line C 511, i.e. the distance between lines 512 and 513, represents an estimate of the Forefoot Width (FW).

Figure 6:
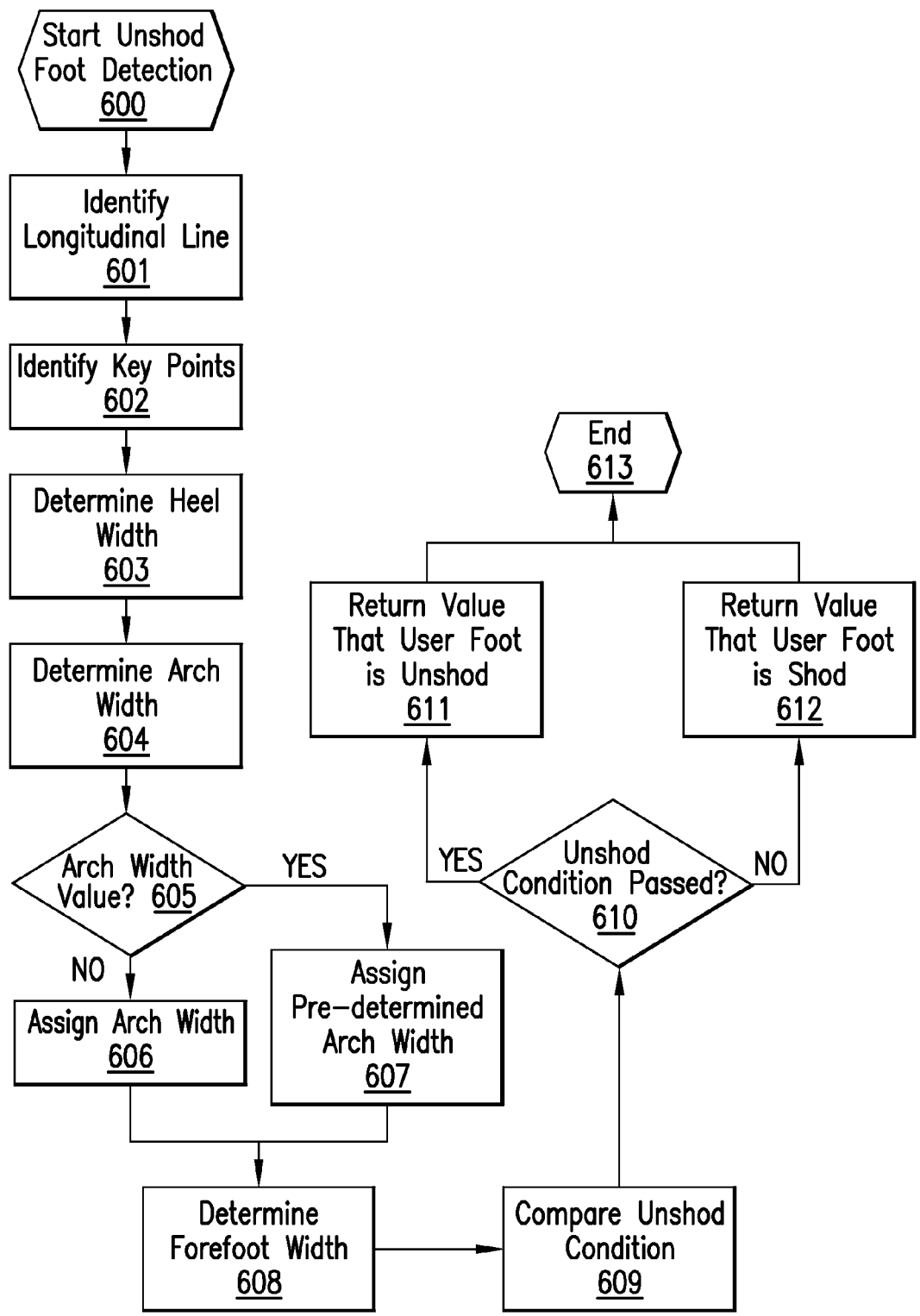
FIG. 6 illustrates an example procedure using foot dimensions from FIG. 5 to determine whether an unshod foot is on a pressure mat, according to an example embodiment of the present invention.

FIG. 6 illustrates an example procedure using foot dimensions from FIG. 5 to determine whether an unshod foot is on a pressure mat, according to an example embodiment of the present invention. In 600, a pressure map may be generated at the start of the unshod foot detection. As explained previously, the pressure map may be generated from collecting a static pressure for a prescribed period of time. In 601, the longitudinal line 500 is identified. In 602, key points are identified, in particular point A 506, point B 507, and point C 508. In 603, the estimated Heel Width may be determined, as explained in FIG. 5 relating to deriving Line A 509. In 604, the estimated Arch Width may be determined, as explained in FIG. 5 relating to deriving Line B 510. In 605, if there is no intersection with the pressure map, then in 607, the Arch Width is assigned a pre-determined number, e.g. some constant that is not zero to avoid the situation where a number could be divided by zero. If the Arch Width does have a value, then in 606, the Arch Width is assigned that value, in 608, the Forefoot Width may be determined, as explained in FIG. 5 relating to deriving Line C 511. In 609, the values previously recorded are compared with pre-determined values. The pre-determined values can be derived by recording and comparing values of actual test subjects wearing shoes and comparing them measurements while standing unshod. For both feet, an example condition is $$(FL/HW \geq FL\_low) \,\&\, (FL/HW \leq FL\_high) \,\&\, (FW/HW \geq FW\_limit) \,\&\, (AW/HW \geq AW\_limit)$$

In this example, FL_low=3.5; FL_high=6.0; FW_limit=1.2; AW_limit=0.1.

In 610, after the condition is determined, if the condition is "true" then, in 611, the person is recognized as being unshod. If the condition is false, then in 612, the user is recognized as wearing shoes. It may be appreciated that values can be added to the condition range to have the option to determine if a person is wearing socks. The procedure to determine if an unshod foot is on a pressure sensor ends in 613.

The target ratios and constant values may be derived by comparing the ratios to actual test subjects and calculating whether the ratios and constants match, on average, the ratios for those test subjects. However, it the ratios may also be altered by adjusting the point of Line A 509, Line B 510, or Line C 511 on varying degrees along the foot length line. The locations of these varying lines are derived from testing multiple subjects and calculating ranges with the least errors. Alternative measurements may allow the lines to vary or in fact to add further lines. For example, a Line D may be added between Line A 509 and Line B. Ratios of Line D compared to the other widths and lengths may also create a new constant with which to compare the ratio. This new constant may be a floor or minimum or a ceiling or maximum constant when compared to the ratio of Line D to a measurement of the length, width, arch width, some other newly derived line, etc.

Figure 7:
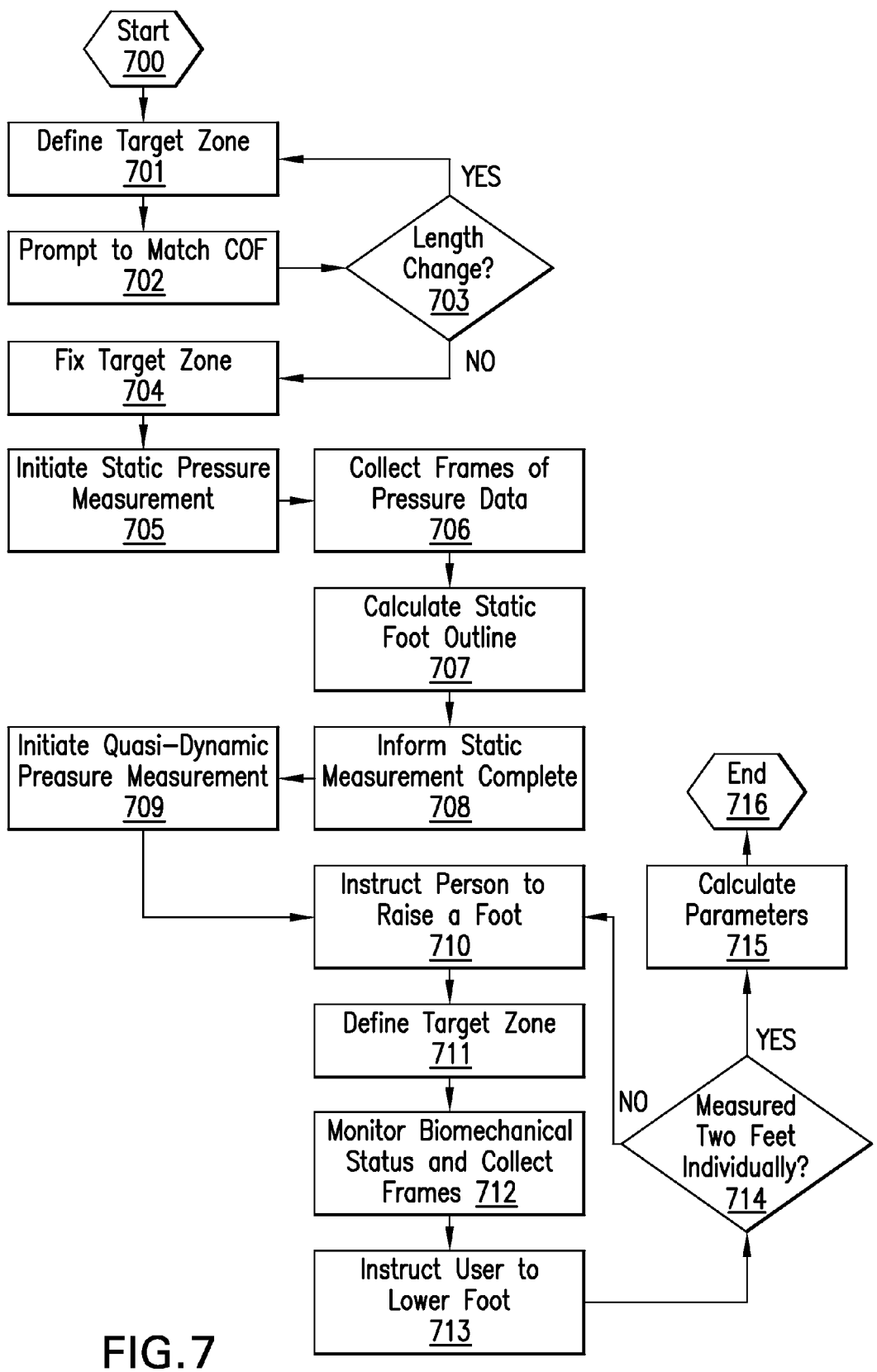
FIG. 7 illustrates an example procedure to take pressure measurements to calculate biomechanical data estimates, such as those in FIG. 2, according to an example embodiment of the present invention.

FIG. 7 illustrates an example procedure to take pressure measurements to calculate biomechanical data estimates, such as those in FIG. 2, according to an example embodiment of the present invention. In 700, the procedure may begin after a person's feet are on pressure measurement sensors. At the start, various other checks may also be performed to interact with a person that is being measured. For example, an output may display a real-time pressure map as soon as a person steps on a pressure mat; a person may be prompted to remove their shoes and step on the pressure mat at designated areas on the pressure mat with their weight balanced between the left and right, front and back; the person may be prompted to indicate whether or not the person is ready for measurement, such as by choking on a "Start" button. Several error checks may have been performed at the pressure measurement collection time, such as to determine whether an unshod foot is actually on the sensor as in FIG. 6, or whether there are other errors with foot alignment, weight, etc. as in 408 or 410 in FIG. 4.

In 701, a target zone may be defined. The target zone may be the geometric center of the pressure print of both feet, but may also be another geometric pressure point of reference. In determining the target zone, the target zone may be shifted 10% distally to force the user to lean forward slight, and consequentially, allow the person's toes to have direct contact with the pressure mat. In 702, a person may be prompted to match the person's center of force (COF) into the target zone. The center of force may be determined by calculating the moment of torque for each sensor point and taking the centroid weighted by the force at each point to create an overall representation of the force of both magnitude and location of the various forces. The center of force may be used to indicate the body's center of gravity.

In 703, if the length of the foot pressure map changes by more than 15 mm, approximately a 2 sensel element difference, 701 is repeated and the target zone may be re-calculated and displayed to the person on an output device. The length of pressure map change that would trigger a re-calculation of defining a target zone may depend on the use of the measurement. A 15 mm threshold is approximately 2 shoe sizes and may justify a re-calculation. The person may be prompted to continue to match the person's COF into the new target zone. If in 703, there is no significant increase of foot pressure length, the initial target zone may not be re-calculated. In 704, the final target zone may be located at a fixed location unless the person moves or lifts his feet. In alternative embodiments, the target zone may also be determined dynamically, wherein the COF matches a dynamic target zone, which may be defined as the center of area.

In 705, a static pressure measurement may be initiated. Frames may be collected at different rates. Pressure data may be collected at a rate of 10 frames per second. While frames are taken, the target zone may be displayed on an output device. In 706, frames of pressure data may be collected. Depending on the desired accuracy of pressure measurements, a minimum number of frames may be needed, such as 20 frames of pressure data. Twenty frames of pressure data at 10 frames per second may require a person to hold a target zone for 2 seconds.

Among the frames collected, some of the frames may have be poor. Some frames may be eliminated for use through a qualifying process. The qualifying process may use any number of different methods. For example, the method described in FIG. 6 for determining whether a foot is unshod may also be used to determine whether a frame is a qualifying frame. If a foot is determined to be unshod, the frame would be qualified. If the frame would not be qualified as unshod, it is likely that the collected frame was poor or that there was an error and would thus be eliminated. Another example method may be to determine whether the balance of weight between the front and back and the sides are properly distributed based on the COF.

In 707, based on the pressure measurements taken, a static foot outline (SFO) may be derived from the pressure measurements. In 708, after static pressure measurements have been taken, the person may be informed that the static pressure measurement has been completed.

In 709, the quasi-dynamic pressure measurement process may commence. Generally, dynamic measurements are taken during ambulation in order to determine pressure on various parts of the person based on his or her gait. However, a quasi-dynamic process estimates the types of pressures created without a need for ambulation. Rather, a quasi-dynamic process may allow for pressure measurements to be taken while a person is standing on one foot in order to simulate pressure that may be generated during ambulation.

In 710, the person may be prompted to hold a balance, such as by holding a balance bar or to keep their balance on their own, and then to gently and slowly lift one foot while balancing and standing on a first planting foot. In 711, a target zone may be defined for the first planting foot based in part on the static foot outline previously determined in 707. The location of the target zone may be slightly modified according to the one-foot pressure map. The user may be prompted to match the target zone for the first planting foot.

In 712, the biomechanical status of the person may be monitored and different triggers for pressure frame collection may be implemented. For example, one trigger to start collecting pressure frames may be when the COF enters the target zone and is stable for a short pre-defined period, such as one second. Again varying number of frames may be collected; for example, 20 frames at 10 frames per second may be collected. An alternative trigger may be to collect frames when the load on the planting foot reaches 90% bodyweight. It may be appreciated that variations and combinations of biomechanical status may trigger the collection of frames. For example, frame collection may be triggered when a person's COF matches the target zone and at least 95% of static weight is achieved. In 713, once the measurement collection is completed, a person may be instructed place replace the raised foot back onto the pressure mat.

In 714, if both feet have been measured individually, parameters may be calculated in 715. If not, 710 to 713 may be repeated to collect frames for the second planting foot. The order of the frame collection of the individually feet may be altered. During the second round of 710, when measuring the second planting foot, the SFO may need to be rotated to match the pressure print of the second planting foot. In 711, a new target zone may also be defined based on the SFO. The location may also be slightly modified according to the one-foot pressure map.

In 715, based on the static or quasi-dynamic pressure measurements from the collected frames, biomechanical data estimates of the foot may be calculated. Only the qualifying frames are used to calculate biomechanical data estimates. Determining qualifying frames may involve methods previously mentioned, such as using the method of determining whether a foot is unshod. The qualifying process is generally performed before the biomechanical data estimate calculations are performed because otherwise the processing would be wasted if a frame were discarded in the qualifying process. Nevertheless, the order of qualifying and calculating biomechanical data estimates may be altered. For example, qualifying may be done for all frames and then calculations of biomechanical data estimates may be done for remaining frames, or vice versa. Alternatively, the combination of the qualifying process and calculation of biomechanical data estimate may be done for each frame at a time.

Using FIG. 2 as a reference for the calculation of biomechanical data estimates, a foot length 201 may be determined by searching along the longitudinal axis and determining the lowest and highest points. The distance between the most posterior point of the heel 204 and the most anterior point 213 may be calculated as the foot length 201. A general foot profile may be used to match the pressure map, similar to the methods described in FIG. 5. A lateral center point of the second toe 211 and a lateral center of the heel 212 may be derived from the foot template and a longitudinal line may be derived which is a line between the two points. The longitudinal line becomes the axis of the searching direction.

Using the pressure maps, the toe line 203 may be determined by searching for the peaks and valleys of pressure. For example, the big toe is known to have a large peak in pressure and valleys in pressure exist between the toes. The distance between the toe line 203 and the most posterior point of the heel 204 is the distance of line L 205. The total area of the foot within line L of the foot is the foot body, consisting of the sums of the areas of sections A 208, B 209, and C 210. Based on the location of pressure, the area of A 208, B 209, and C 210 may be calculated. The Arch Index is equal to B divided by the area of the foot body. The arch index of a person's foot may then be the average arch index of all the qualified frames for each foot.

The biomechanical data estimates may include foot dimensions, estimated foot type, and estimated body weight. For example, biomechanical data estimates that may be calculated may include peak pressure maps of both static and quasi-dynamic pressure, an artificial double-footed peak pressure map derived from the combined left and right foot quasi-dynamic foot pressure measurements, foot length, foot width, body weight, a longitudinal line, an arch index, etc. The biomechanical data estimates may be stored in the kiosk storage area or sent over a network to be stored. Demographic information, for example, information relating a user id number associated with corresponding biomechanical data estimates and a recommended footcare product, may be stored in a storage device or relayed over a network for storage in a central database or server.

FIG. 8a illustrates an example decision matrix, according to an example embodiment of the present invention. A decision matrix module is used to correlate classified subgroups with a footcare product model. The decision may, in part, be derived from the various footcare products available, and may thus vary based on the product specification list that is stored in the storage area. The classified subgroups may be based on biomechanical data estimates or directly on the pressure measurements themselves. Another example of selecting a footcare product is a mapping between a classified subgroup and footcare products.

A set of 14 pre-manufactured orthotics may be provided as described in concurrently filed application titled, "Cushioned Orthotic", application Ser. No. 11/524,979, filed Sep. 21, 2006. These orthotics include 4 lengths/size, 2 different levels of arch support and 2 different levels of cushioning. However, only one level of cushioning is provided for the largest size. This may be because people of the largest size feet require the maximal cushioning.

The particular matrix in FIG. 8a is divided into bands and indexed by weight of the person and arch index. The bands represent the foot length of the person. For example, in the example matrix there are four bands: Band A 850 for foot lengths below 244 mm, Band B for foot lengths greater than and including 244 and less than 255 mm, Band C for foot lengths greater than 255 mm and less than 270 mm, and Band D for foot lengths greater than and equal to 270 mm. Each band contains a cross-reference between a weight and an arch index.

In the example matrix the weights are divided between low weight and high weight, although with more product models and weights tested the weight categories within a band may increase. The dividing weight between low and high weight is the median weight. The determination of the median weight is the median weight that is expected for people of a particular foot length. The type of support may require more cushioning for people of a certain foot length but heavier than the median weight for that foot length. The median weight would thus vary between the different bands. As foot length increased, a median weight would also be expected to increase.

In the example matrix the arch index is divided between low, medium or normal, and high, although with more product models the arch index may increase in categories. The low arch index range 853 may be defined as greater than 0.257. The medium arch index range 859 may be greater than 0.173 and less than or equal to 0.257. The high arch index range 860 may be less than or equal to 0.173. In these examples, there is an inverse relationship between the arch index and the arch, e.g., the higher the arch index the lower the arch. It is possible for the foot care products to be sold individually for the left and the right foot because it is possible that the right and the left foot will have differing arch indexes. Presumably, the foot length and body weight will not differ. If the footcare product were only sold in pairs, then the low or high arch index would dominate over the medium/normal arch index. For example, if the right foot was a high arch index and the left foot was a normal arch index, the selected model would be for the high arch index. Between the high arch index and the low arch index the more conservative product may be selected, e.g. the medium arch index may be selected.

Using the foot length, arch index, and weight of a person a product model may be selected and then recommended to that person. For example, if a person had a foot length of 220 mm, weighed 120 pounds, and an arch index of 0.261. A length of 220 mm would mean the person would fall within Band A 850. Band A 850 has a median weight 855 of 135 pounds, thus a person weighing 120 pounds would be classified in the low weight 851. An arch index of 0.261 would place the person in the low arch 854 of Band A. A low arch 854 within Band A 850 of low weight 851 would recommend "Product 1" 856. As another example, suppose a person had a foot length of 220 mm, weighed 150 pounds, and had an arch index of 0.205. The foot length as before would fall into Band A 850. Band A 850 has a median weight 855 of 135 pounds, thus a person of 150 pounds would be classified in the high weight 852. An arch index of 0.205 would place the person in the medium or normal arch 858 of Band A. A medium arch 858 within Band A 850 of high weight 852 would recommend "Product 4" 857.

It may be appreciated that while this decision matrix is displayed in this example as a spreadsheet, the organization of the products and biomechanical data estimates may be organized, searched, and accessed in the kiosk storage using other methods, such as an array, linked list, database table, etc.

Figure 8B:
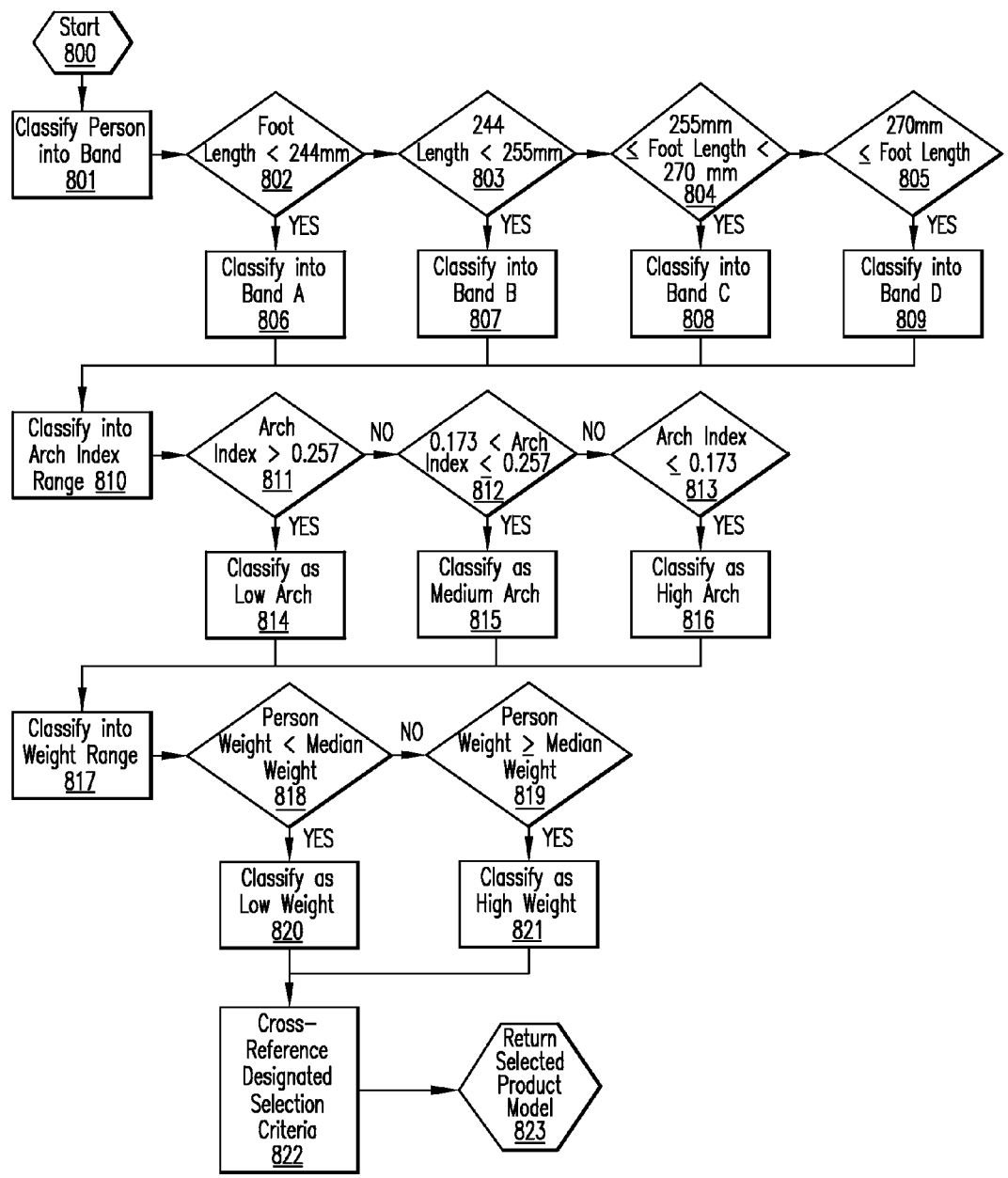
FIG. 8b illustrates an example procedure for selecting a footcare product from a decision matrix, such as in FIG. 8a, based on pressure measurements, according to an example embodiment of the present invention.

FIG. 8b illustrates an example procedure for selecting a footcare product from a decision matrix, such as in FIG. 8a, based on pressure measurements, according to an example embodiment of the present invention. The procedure may be used in selecting a recommended footcare product 414 as in FIG. 4. In 800, when the procedure has started, the person's weight, arch index, and foot length will have already been determined, from the pressure measurements, the scale, or the person's input. In 801, the person is classified into a Band. In 802, if the person's foot length is less than 244 mm the person is classified into Band A in 806. If not, in 803, if the person's foot length is greater than or equal to 244 mm or less than 255 mm the person is classified into Band B in 807. If not, in 804, if the person's foot length is greater than or equal to 255 mm or less than 270 mm the person is classified into Band C in 808. If not, in 805, if the person's foot length is greater than or equal to 270 mm the person is classified into Band D in 809.

After the Band is determined, in 810 the person's arch index may be cross-referenced with an arch index range. In 811, if the person's arch index is greater than 0.257, the person is classified as having a low arch in 814. If not, in 812, if the arch index is greater than 0.173 or less than or equal to 0.257, the person is classified as having a medium arch in 815. If not, in 813, if the arch index is less than or equal to 0.173, the person is classified as having a high arch in 816.

After the person is classified into a Band and Arch Index, in 817 the person is classified into a weight range. In 818, if the person's weight is less than the median weight, the person is into a low weight for the particular band 820. If not, in 819, and by default, if the person's weight is greater than or equal to the median weight, the person is classified into a high weight for the particular band 821. As in FIG. 8a, the median weight may vary depending on the particular band. The order of the designation of the arch index range, weight range, and Band may also vary. For example, depending on how the data is stored or how the software is written, the weight range may be determined before arch index range. After a person is classified based on selection criteria, the selection criteria may be cross-referenced in 822 to determine the recommended product model. This product model is returned in 823 to be recommended to the person.

Figure 9A:
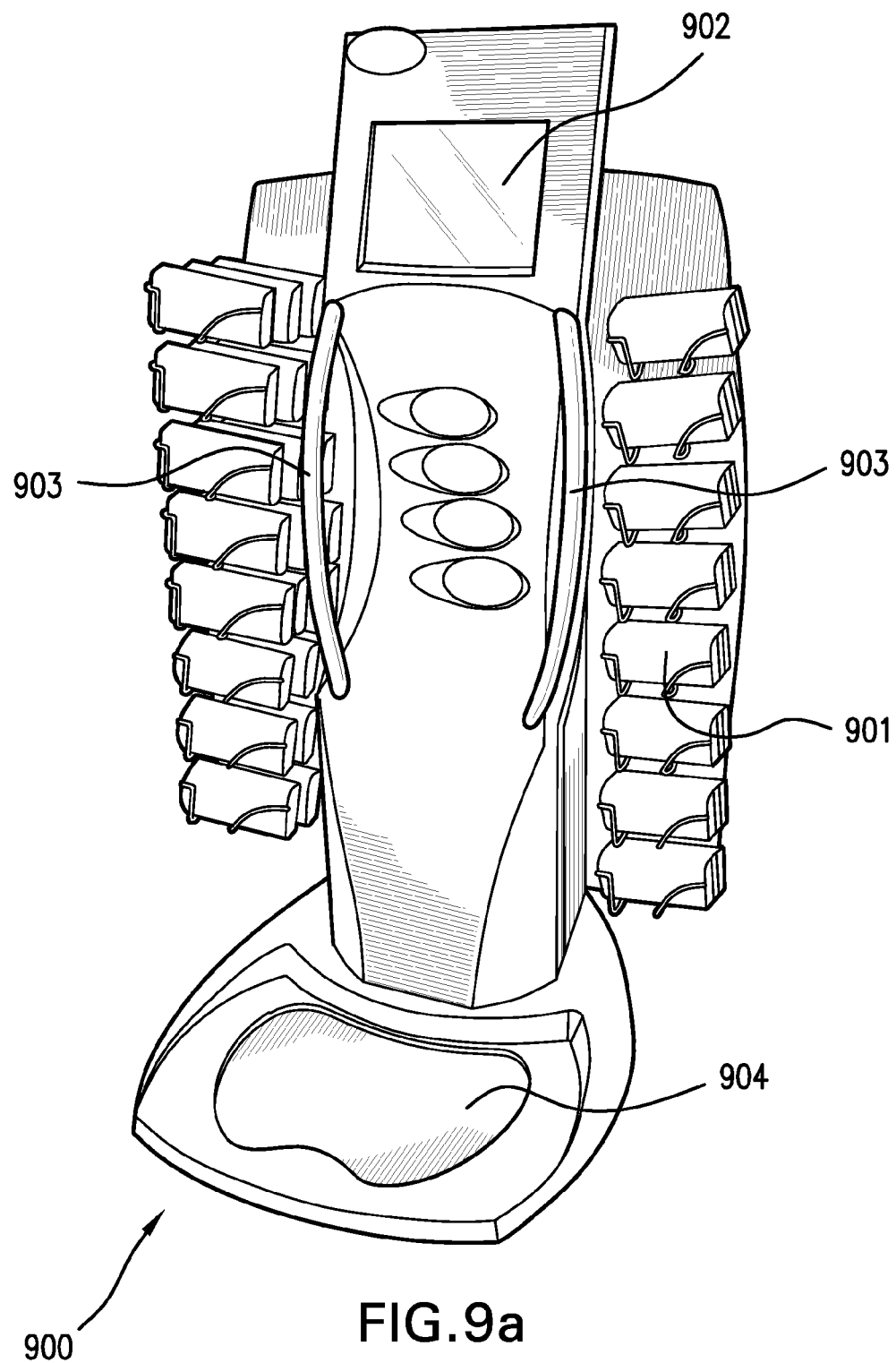
FIG. 9a illustrates an example kiosk selecting pre-manufactured orthotics, according to an example embodiment of the present invention.

FIG. 9a illustrates an example kiosk selecting pre-manufactured orthotics, according to an example embodiment of the present invention. A pressure mat 900 which may be removably attached to the kiosk is located on the bottom of the kiosk. On the surface 904 of the pressure mat 900, alignment marks may be displayed that match the exact pressure map locations. The foam template mat may overlay the pressure sensors in order to guide a person using the kiosk in the placement of the person's feet, and the entire pressure sensor and foam template mat combination may form a pressure mat 900. A set of candidate footcare products, in this example orthotics, may be displayed on or near the kiosk in a merchandise display area 901 located on the sides of the kiosk, e.g. stored in clear plastic shelves that allow removal. Other forms of removable attachments may be used to display products. It may be appreciated that the merchandise display area may be located on the kiosk or near the kiosk. Alternatively, footcare products may be dispensed like that of a vending machine. Handlebars 903 which a person may use to balance while standing on one foot during a pressure measurement procedure may be vertical bars, but in alternative kiosks, handlebars 903 may be located on the sides. An output device 902, such as a touch screen device, may be located at eye-level or where a person standing on the pressure mat 900 may easily access and view the touch screen.

Figure 9B:
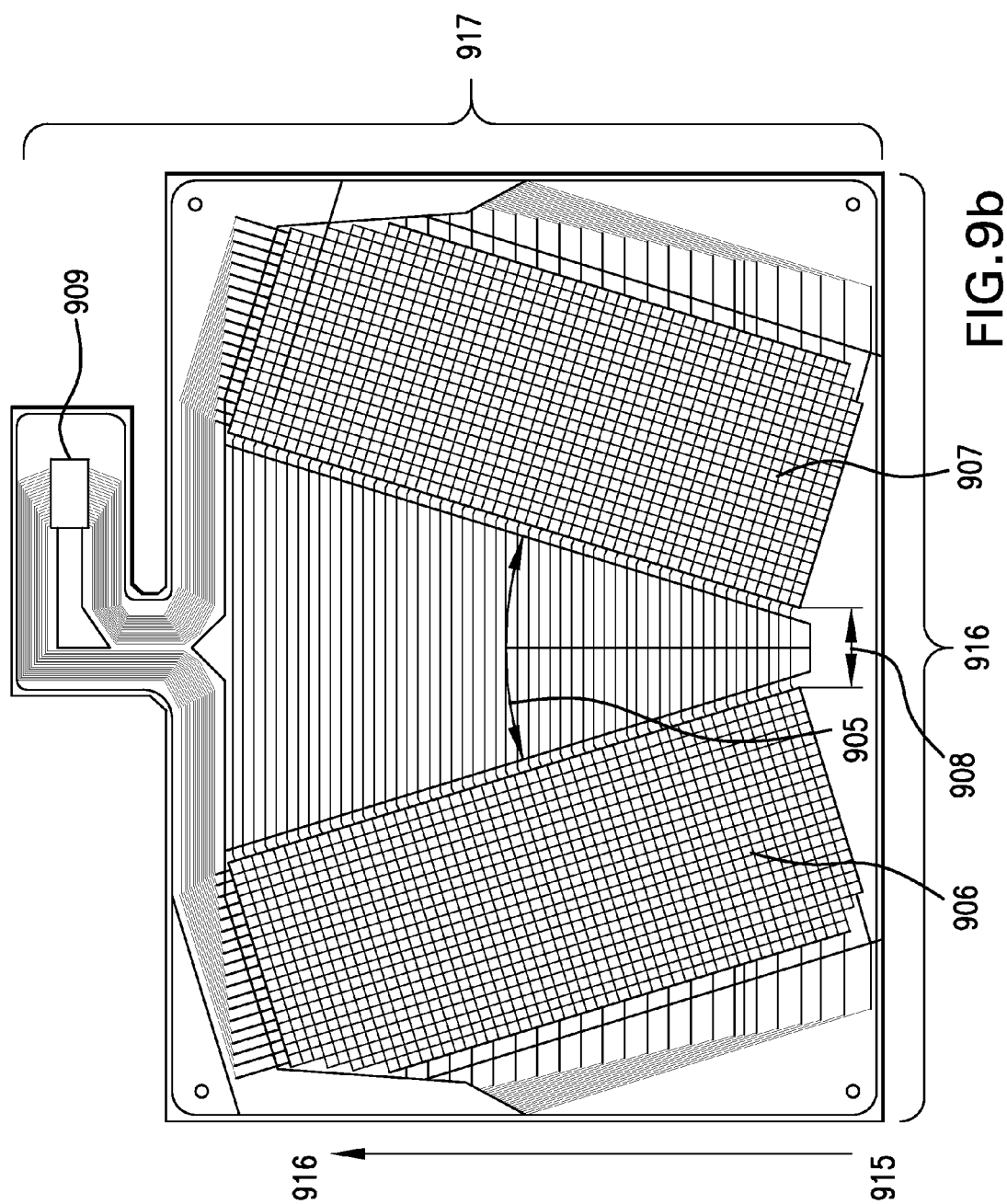
FIG. 9b illustrates an example internal structure of a pressure pad, according to an example embodiment of the present invention.

FIG. 9b illustrates an example internal structure of a pressure pad, such as the pressure pad 900 in FIG. 9a, according to an example embodiment of the present invention. A sensor grid array for the left foot 906 and right foot 907 is separated 908 by 10 cm at the lower-right corner of the left foot sensor grid 906 and the lower-left corner of the right foot sensor grid 907. The angle of separation 905 between the two sensor grids is 17.5 degrees. The layout of the grid is developed for the comfort of the user and is not necessary for measurement. The pressure pad also contains a handle 909. The pressure pad itself is sloped upward at an angle where the point at 915 is at a vertical height lower than the point at 916. The reason for this is because people naturally tend to stand without as much pressure on their toes, and the angle forces the person to create a pressure image. The actual degree of the slope may vary, but a lean of approximately 10% is recommended. The importance of the sensors receiving proper contact from the toes is to ensure a proper reading of the foot length. The width 916 of the pressure mat may be 24 inches and the length 917 is 21.5 inches.

Figure 9C:
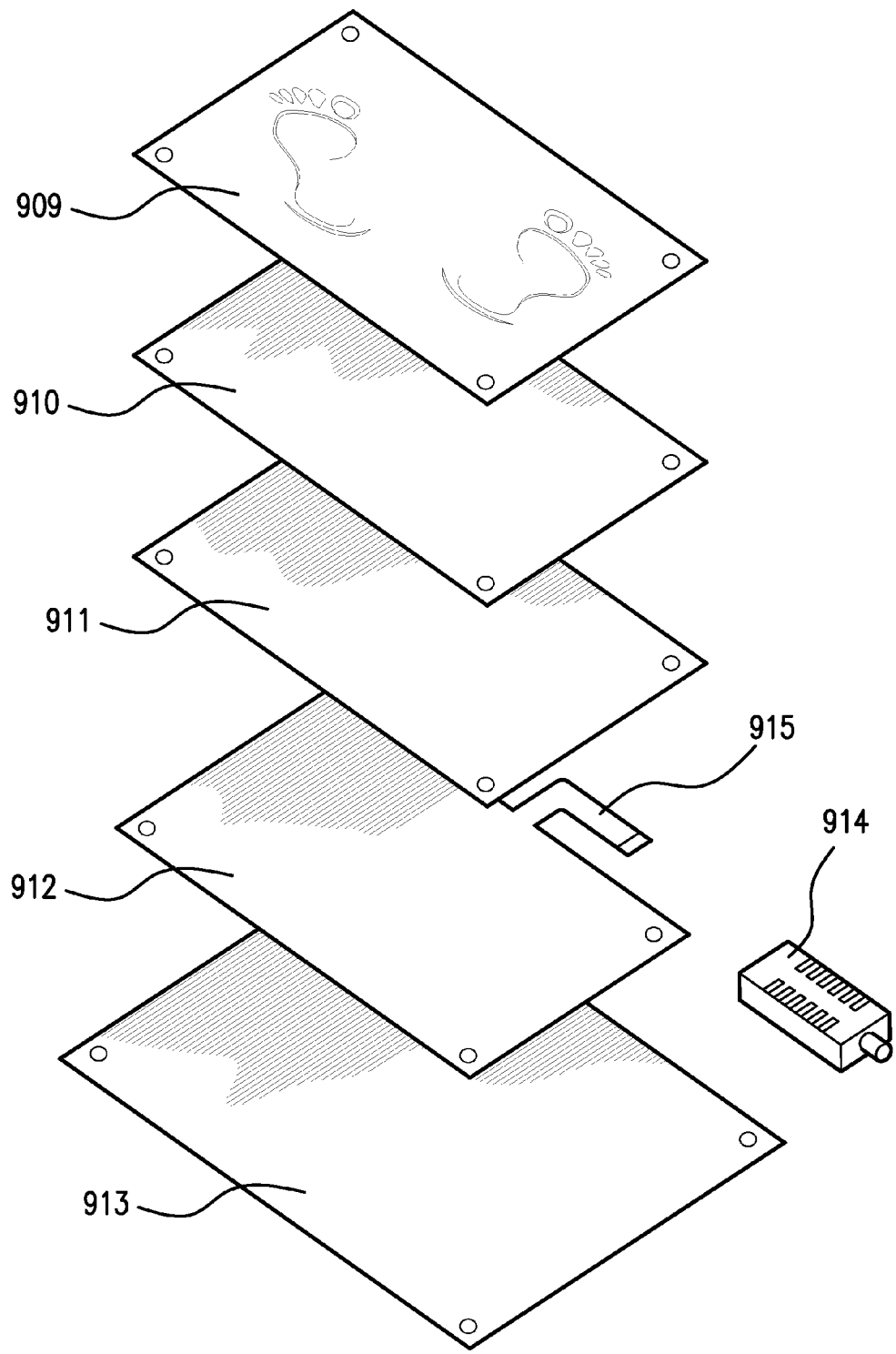
FIG. 9c illustrates an example layer-by-layer internal structure of a pressure pad, according to an example embodiment of the present invention.
Figure 10A:
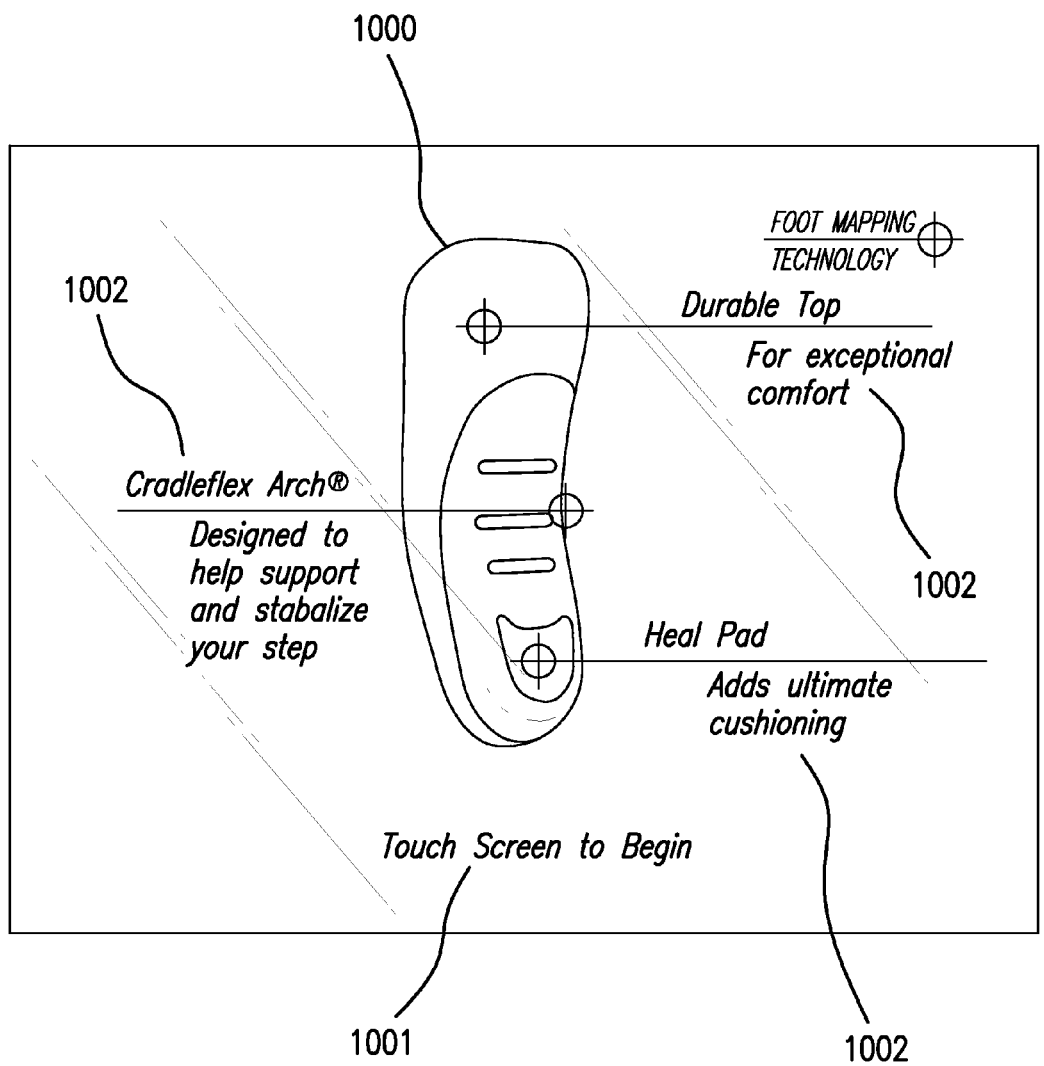
FIG. 10a illustrates an example screen that may display footcare products, according to an example embodiment of the present invention.
Figure 10B:
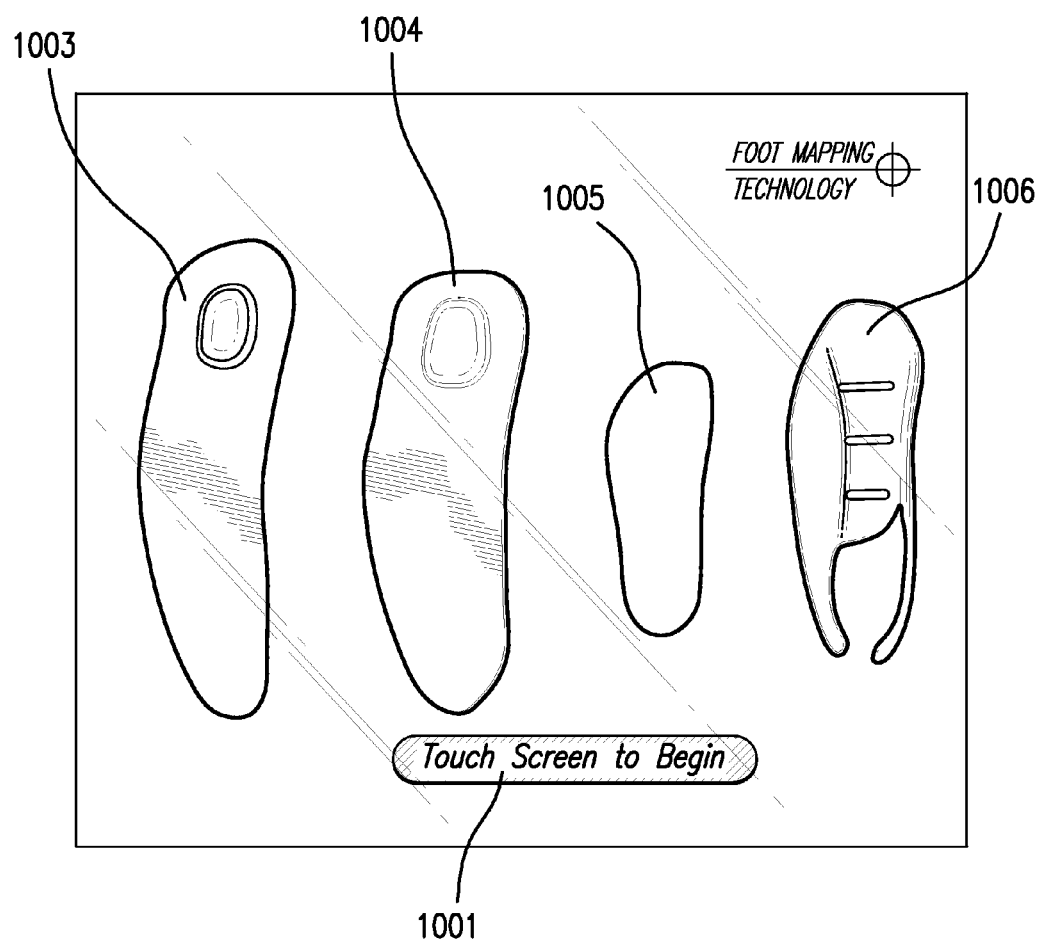
FIG. 10b illustrates an example screen that may display a footcare product and its various components, according to an example embodiment of the present invention.

FIG. 9*c* illustrates an example layer-by-layer internal structure of a pressure pad, such as the pressure pad 900 in FIGS. 9*a* and 9*b*, according to an example embodiment of the present invention. The first layer 909 is the top of the pressure mat and contains an image of the foot outline and boundaries of the foot measurement area, as viewable by a person using the pressure mat. This is also the layer that is in direct contact with the person's feet. The second layer 910 may be a foam sheet that may provide padding for the feet. A third layer 911 may be a teflon sheet, or other non-conductive material. A fourth layer 912 may be the sensor mat containing pressure sensors. Extending from the sensor mat may be a set of leads 915 attached to a handle 914. The bottom layer 913 hard layer supporting the pressure mat and may be made of acrylonitrile-butadiene-styrene (abs). The various layers of the pressure mat may be altered, either in order or in material, depending on various factors, such as the sensitivity of the pressure, comfort level, or height of the pressure mat.

FIGS. 10 through 20 illustrate example screens that may be displayed on an output device while performing the example procedures of FIGS. 4, 7, and 8*b*, according to an example embodiment of the present invention. FIG. 10*a* illustrates an example screen that may display footcare products, according to example 401 in FIG. 4, while the system is not in use, according to an example embodiment of the present invention. An example image 1000 of a footcare product, e.g. a cushion orthotic, in the set of available footcare products may be displayed. Alternatively, a video clip or a rotating image of the product may be displayed. Audio may also be provided along with the image or video. Descriptions 1002 of the displayed footcare product may also accompany the video or image 1000. An instruction 1001 to initiate the kiosk may be displayed as well, e.g. a button reading "Touch Screen to Begin." FIG. 10*b* illustrates an example screen that may display a footcare product and its various components, according to an example embodiment of the present invention. For example, a cover layer 1003, cushioning layers 1004 and 1005, and a bottom shell layer 1006 of a footcare product, like that shown in FIG. 10*a*, may be displayed on a page with an instruction 1001 to initiate the kiosk.

Figure 11:
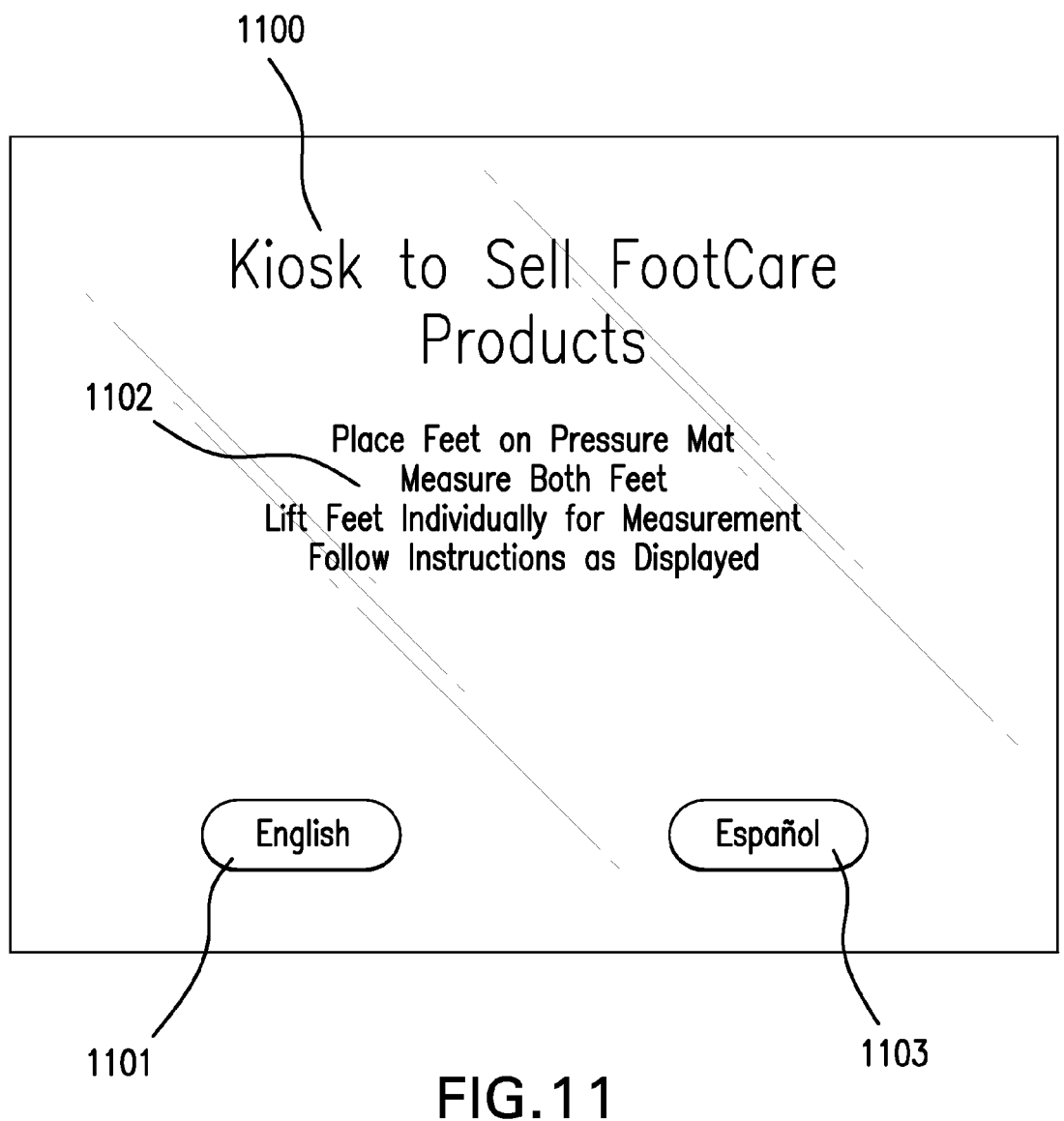
FIG. 11 illustrates any number of example screens that display information, instructions, or that provide a language option, according to an example embodiment of the present invention.

FIG. 11 illustrates any number of example screens that display information, instructions, or that provide a language option, according to examples 403 and 406 in FIG. 4, according to an example embodiment of the present invention. For example, a title 1100, which may contain the name of the system or the name or trademark of the company employing the kiosk, may be listed on the screen. Instructions 1102 on how to generally use the kiosk may also be displayed. A language option may be presented, e.g. the user may choose English language 1101 or Spanish language 1103 instructions. Alternatively, a "switch to Spanish" option may be displayed where the default may be English language instructions, or vice versa. It may be appreciated that other languages may be accommodated by adding language files to the kiosk.

Figure 12:
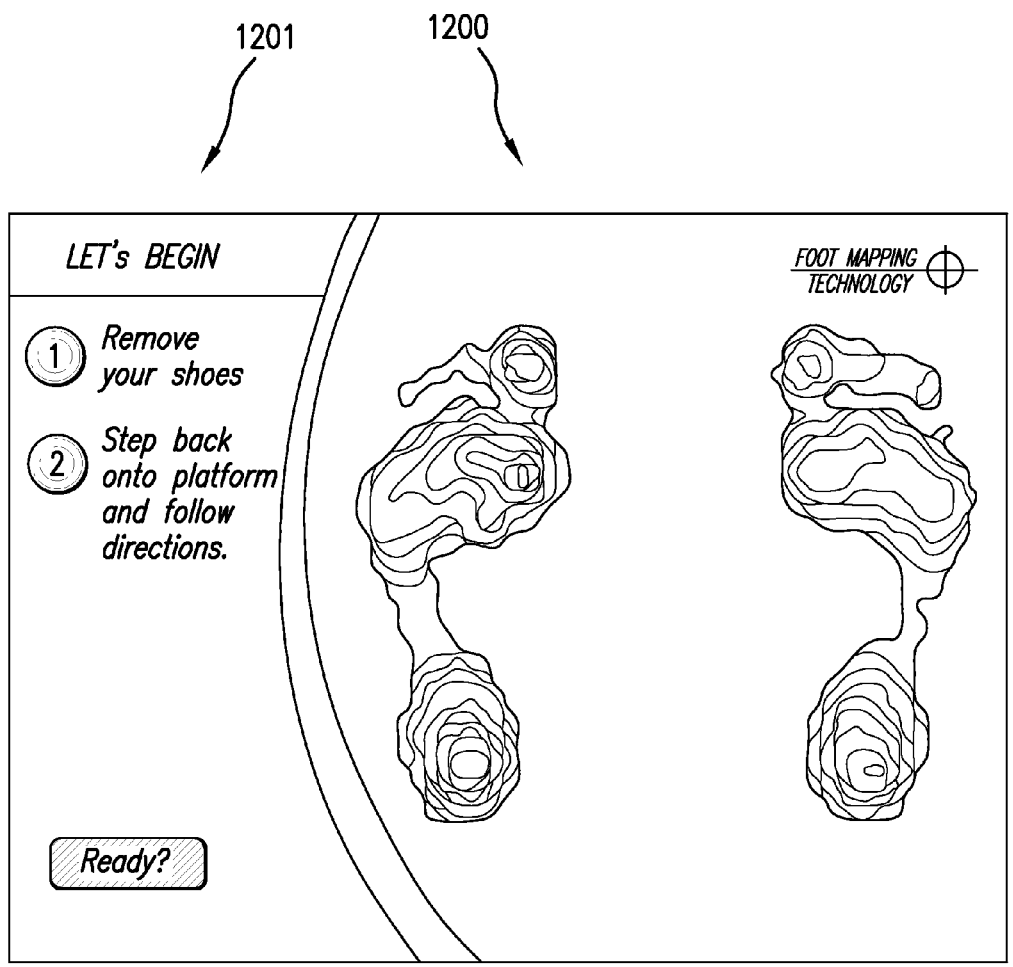
FIG. 12 illustrates an example instruction screen directing a person to take off his or her shoes, according to an example embodiment of the present invention.

FIG. 12 illustrates an example instruction screen directing a person to take off his or her shoes, according to an example embodiment of the present invention. The screen may show a real-time pressure map 1200 of the person's feet. Instructions 1201 may be displayed on another side of the screen. At the direction of the instruction screen, a person may take off his shoes and step back onto the pressure mat. An error check may be performed using a procedure to determine whether an unshod foot is on the pressure mat, such as the example procedure of FIG. 7. Moreover, error checks may be performed, such as those described in 410 of FIG. 4. Subsequent error checks may be performed on any subsequent screens as well. If an error is detected, the person may be prompted to restart the procedure, or further instructions or more detailed instructions may be displayed to help the person rectify any errors.

Figure 13A:
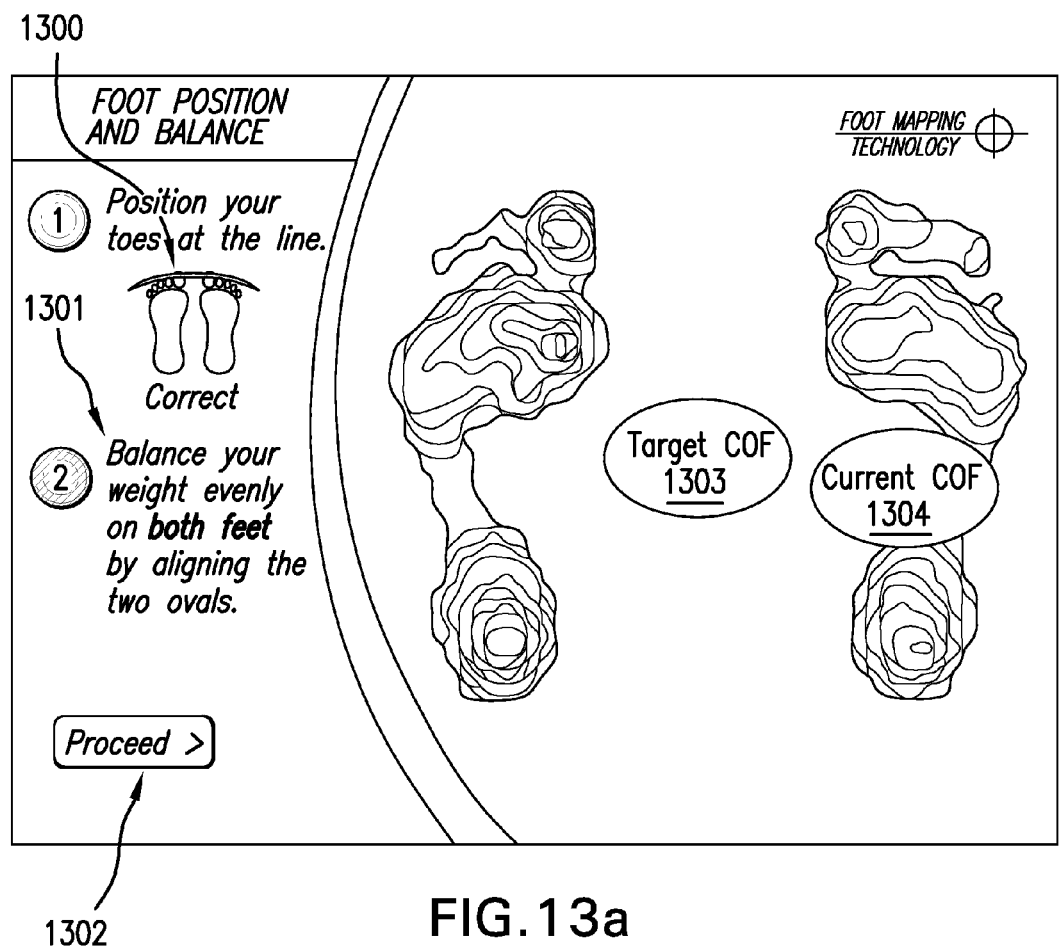
FIG. 13a illustrates an example screen that may be displayed to a person to help achieve proper foot alignment and weight distribution, according to an example embodiment of the present invention.

FIG. 13*a* illustrates an example screen that may be displayed to a person to help achieve proper foot alignment and weight distribution, according to an example embodiment of the present invention. Foot alignment may be determined according to analysis of foot measurements, e.g. analysis of foot pressure measurements as described above in example 408 in FIG. 4. A person may be asked to position his or her toes at a line 1300, and a corresponding line may also appear on the pressure mat to guide the person to stand in the appropriate position. A target Center of Force 1303 and a current Center of Force 1304 oval may be displayed on the screen. Further instruction may request that the person balance his or her weight evenly on both feet by aligning two displayed ovals 1301 (in alternative embodiments circles or other shapes may be displayed). As the person shifts his or her weight, the COF is recalculated and the COF oval moves on the screen. While the weight is unbalanced, the person may be unable to proceed to the next step because a "proceed" button 1302 may not be active.

Figure 13B:
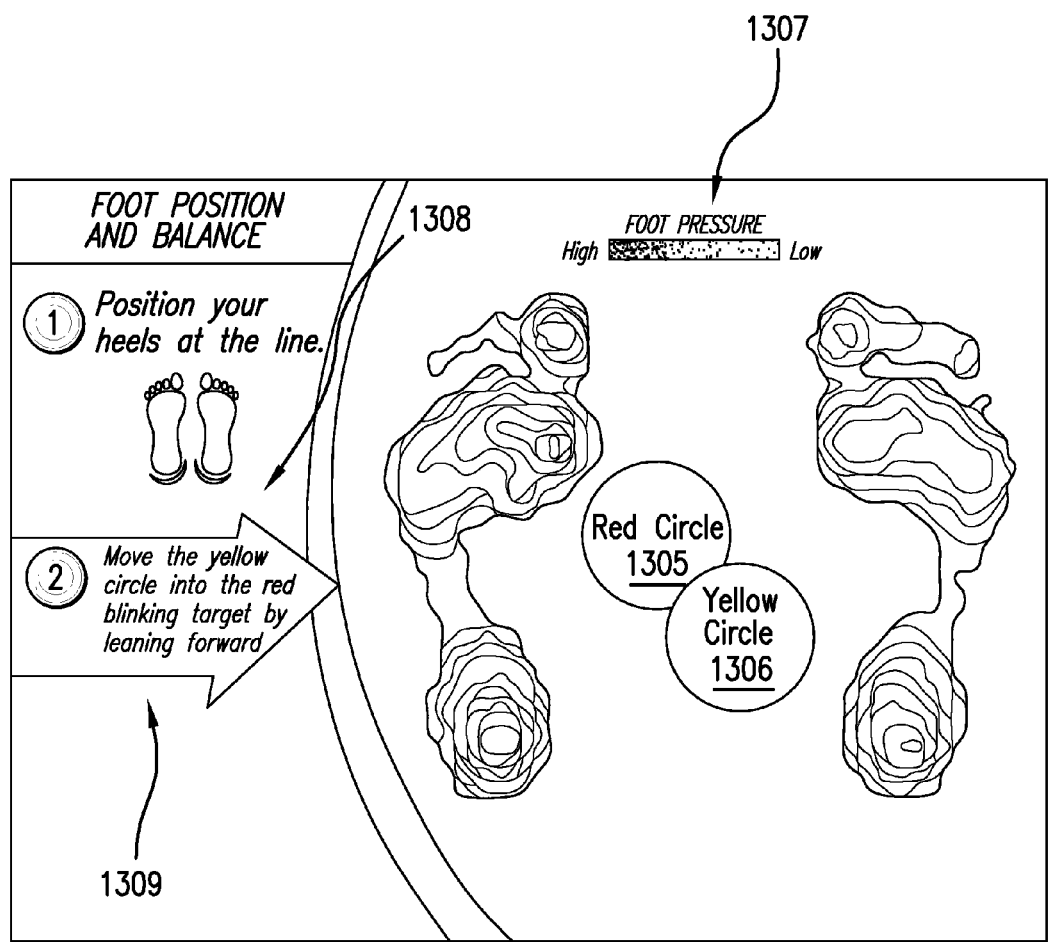
FIG. 13b illustrates an alternative example screen that may be displayed to a person to help achieve proper foot alignment and weight distribution, according to an example embodiment of the present invention.

FIG. 13*b* illustrates an alternative example screen that may be displayed to a person to help achieve proper foot alignment and weight distribution, according to an example embodiment of the present invention. Alignment marks in the anterior of the feet may be replicated on the screen as the anterior limit 1308 of the measurement boundary. A foot pressure gauge 1307 may be displayed to allow the user to interpret the pressure results. The person may be instructed 1309 to move a yellow circle 1306 into a red target circle 1305, similar to the example in FIG. 13*a* where a person may be asked to move a current COF to a target COF.

Figure 14:
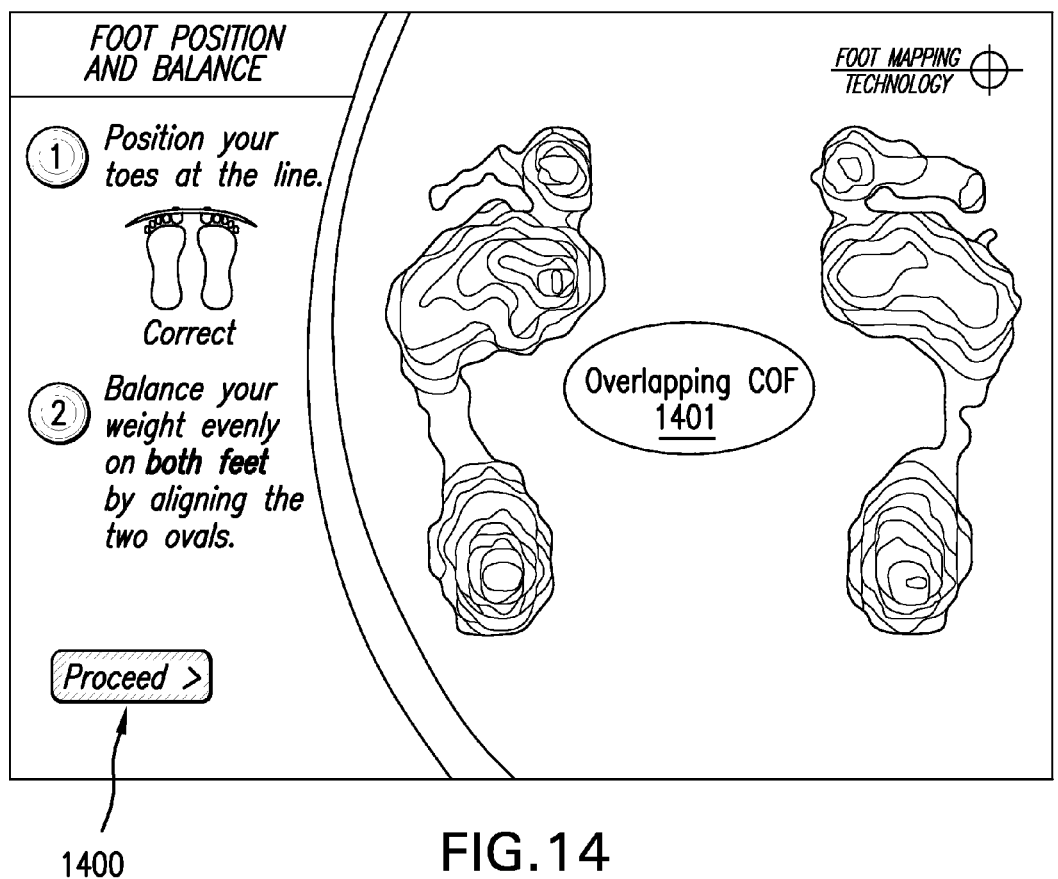
FIG. 14 illustrates an example screen that may be displayed to a person when the person has his or her weight balanced on both feet, according to an example embodiment of the present invention.

FIG. 14 illustrates an example screen that may be displayed to a person when the person has his or her weight balanced on both feet, according to an example embodiment of the present invention. An active "proceed" button 1400 may be highlighted as active after the weight is balanced. This may be indicated if the Current COF and Target COF oval become an overlapping balanced COF 1401. Measurements may be obtained, for example, in a procedure described in 411 of FIG. 4, or illustrated in more detail in 705 to 708 of FIG. 7.

Figure 15:
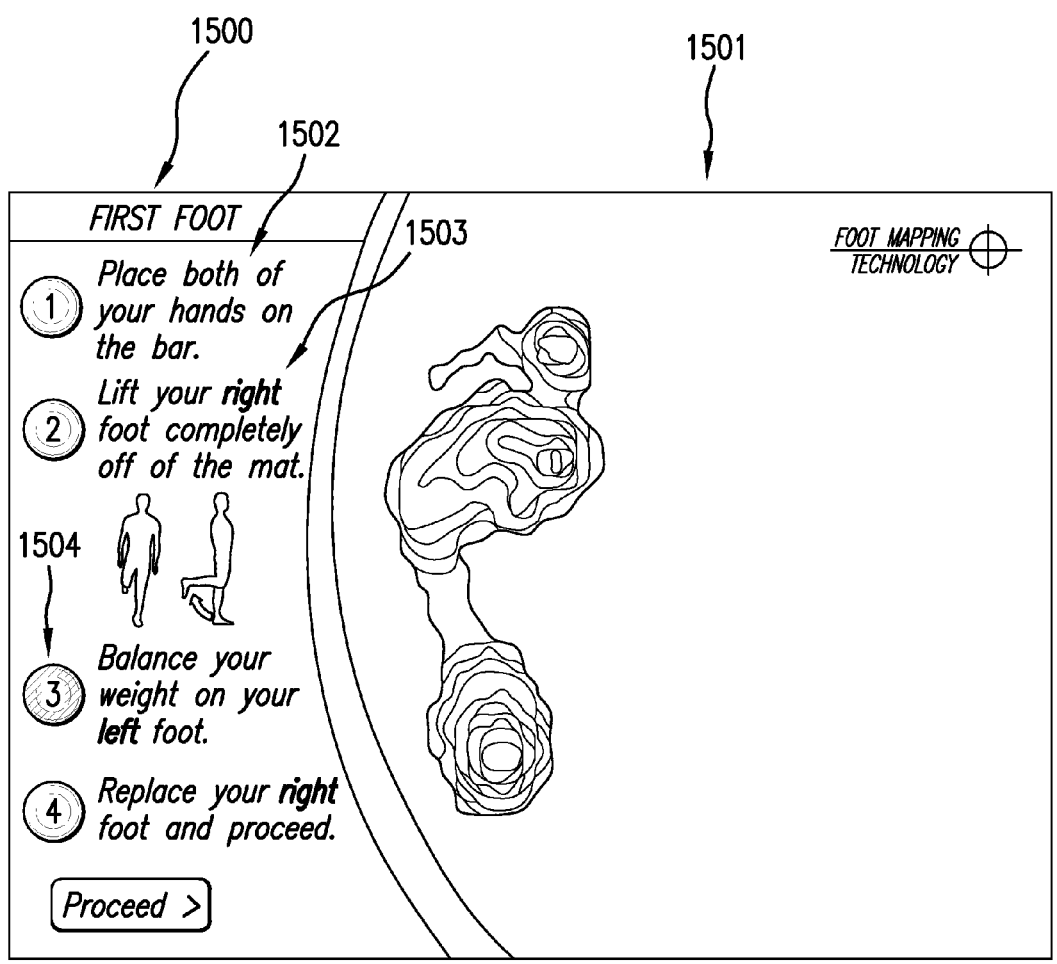
FIG. 15 illustrates an example screen containing instructions that may be displayed to a person regarding taking quasi-dynamic foot measurements, according to an example embodiment of the present invention.

FIG. 15 illustrates an example screen containing instructions that may be displayed to a person regarding taking quasi-dynamic foot measurements, e.g. pressure measurements of the person while the person stands on the left foot, according to an example embodiment of the present invention. Instructions 1500 may be displayed in one section and various steps may be highlighted as they are performed. A first instruction 1502 may request that the person place his or her hands on a bar for balance and safety purposes. The person may hold onto bars, such as those of 903 of the example kiosk illustrated in FIG. 9. The bars may contains sensors that may register contact in order for a kiosk to determine when this step has been performed. A second instruction 1503 may instruct the person to slowly raise the right foot completely off the pressure mat. A third instruction 1504 may instruct the person to balance his or her weight on the remaining left foot, in this case the first planting foot. These three instructions may be implemented according to example 707 to 709 of FIG. 7. Pressure measurements may be taken while the person is standing on the left foot. While pressure measurements are collected, a pressure map of the first planting foot 1501, in this case the left foot, may be displayed on the screen.

Figure 16A:
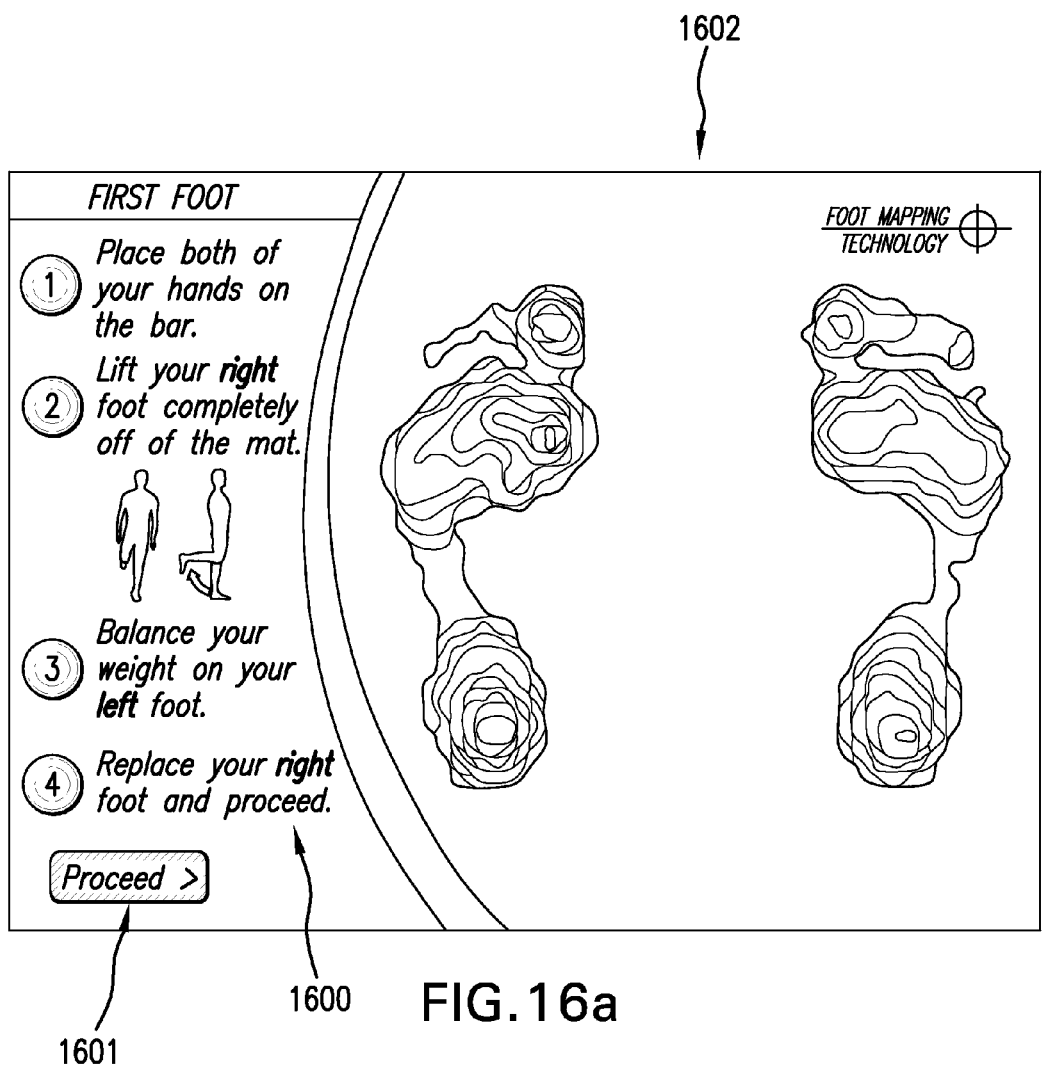
FIG. 16a illustrates an example screen that may be displayed after measurements of a single planting foot are taken, according to an example embodiment of the present invention.

FIG. 16*a* illustrates an example screen that may be displayed after measurements of a single planting foot are taken, according to an example embodiment of the present invention. An instruction 1600 may be highlighted after measurements have been taken to indicate that the person's foot may be placed back onto the pressure mat. When the person's foot is detected on the pressure mat, the real-time pressure map 1602 may display the foot that was previously lifted off the mat, in this example the right foot. This may be done according to example 710 in FIG. 7. When measurements are completed and the foot is replaced, a "proceed" button 1601 may be activated to indicate to a person that the measurements of the left foot were taken.

Figure 16B:
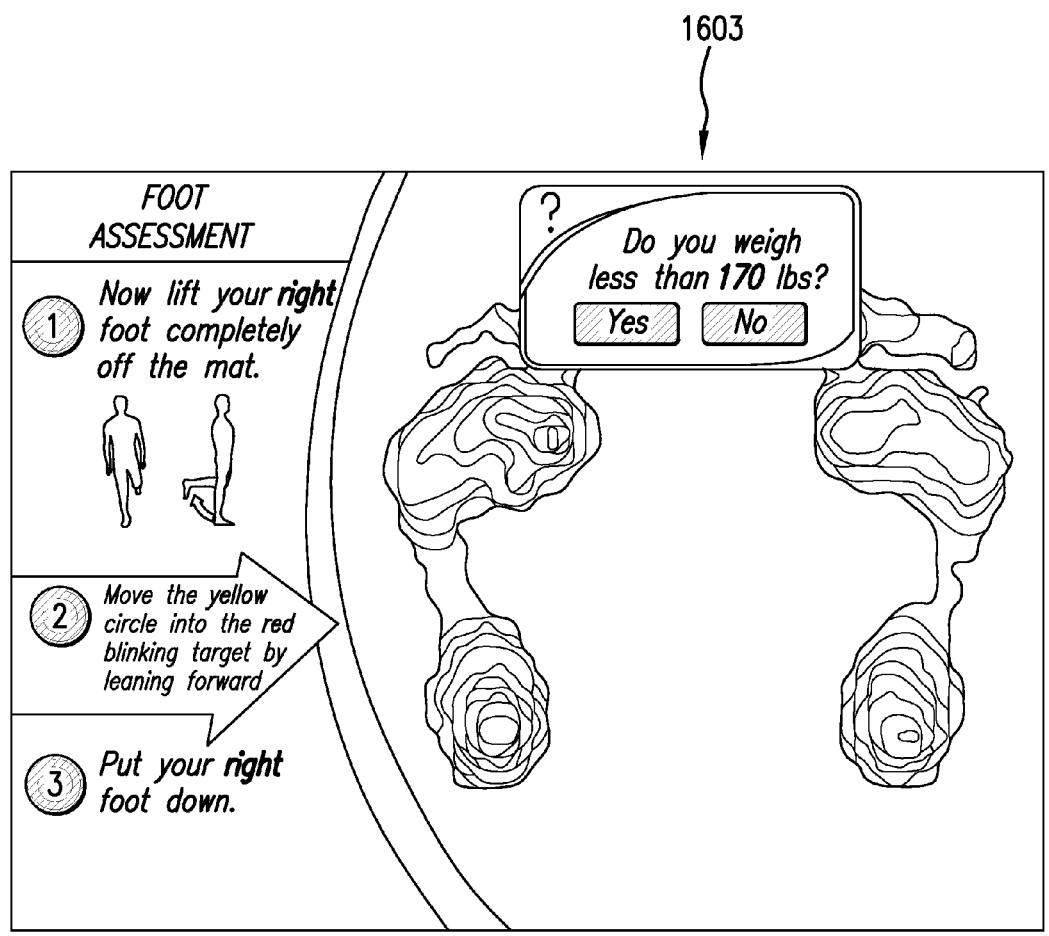
FIG. 16b illustrates an alternative example screen that may be displayed after measurements of a single planting foot are taken, according to an example embodiment of the present invention.

FIG. 16*b* illustrates an alternative example screen that may be displayed after measurements of a single planting foot are taken, according to an example embodiment of the present invention. In the example screen, after the foot is placed back on the mat the person may be prompted for a weight input 1603 asking whether the person weighs less than a pre-defined weight. The pre-defined weight may be derived from a median weight of a particular band, for example, of a band as shown in FIG. 8*a*. The screen at which the user is asked to input weight may be displayed at any point of the measurement process. For example, the prompt for a weight input may be shown after both feet have been measured individually, before any feet have been measured, etc. Alternatively, the prompt may not be displayed at all if the pressure measurements are deemed accurate enough to calculate the weight, or if an optional scale is used to verify the pressure measurement's weight calculation.

Figure 17A:
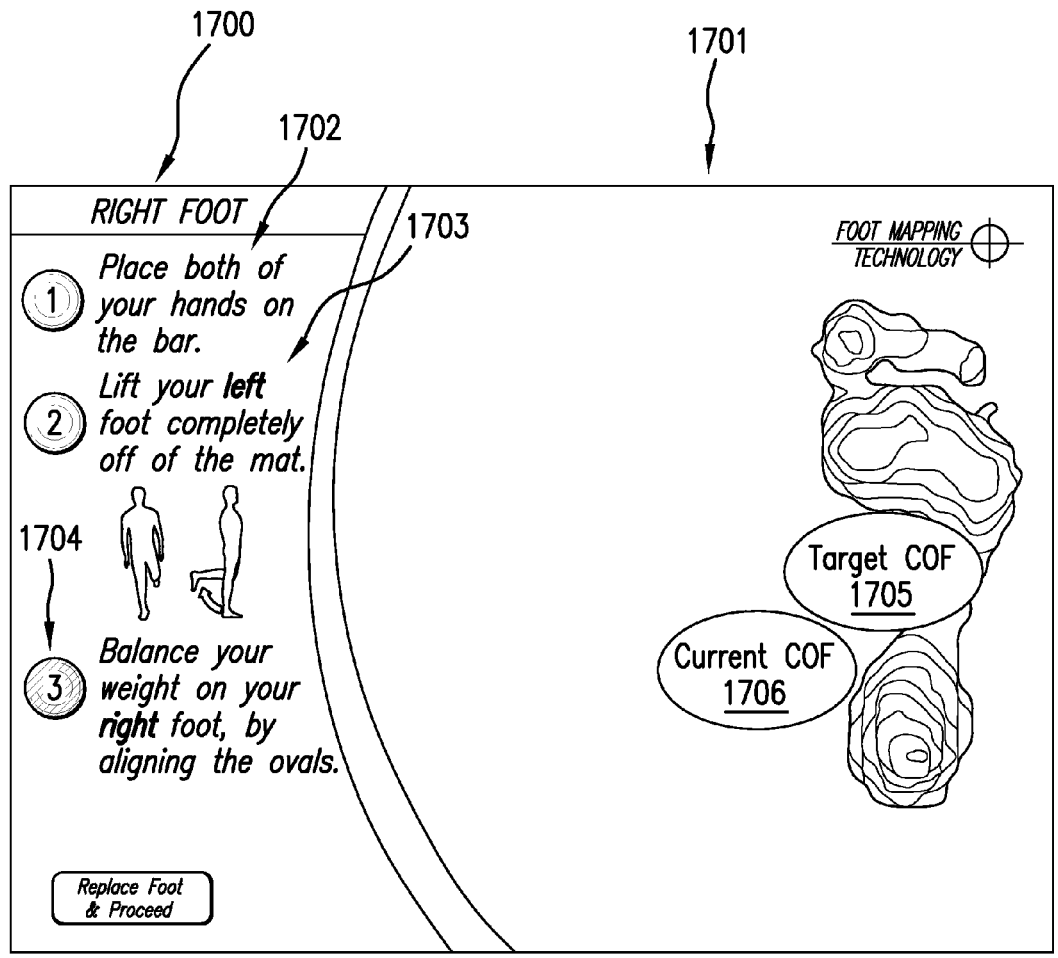
FIG. 17a illustrates an example screen containing instructions that may be displayed to a person regarding taking pressure measurements of the person while the person stands on the right foot, according to an example embodiment of the present invention.

FIG. 17*a* illustrates an example screen containing instructions that may be displayed to a person regarding taking pressure measurements of the person while the person stands on the right foot, according to an example embodiment of the present invention. Instructions 1700 may be displayed in one section and various steps may be highlighted as they are performed. A first instruction 1702 may request that the person place his or her hands on a bar for balance and safety purposes. The person may hold onto bars, such as those of 903 of the example kiosk illustrated in FIG. 9. The bars may contains sensors that may register contact in order for a kiosk to determine when this step has been performed. A second instruction 1703 may instruct the person to slowly raise the right foot completely off the pressure mat. A third instruction 1704 may instruct the person to balance his or her weight on the remaining right foot, in this case the planting foot, by aligning the ovals, for example, a current COF oval 1706 with that of a target COF oval 1705. These three instructions may be implemented through the repeated 707 to 709 of FIG. 7. Foot measurements, e.g. pressure measurements, may be taken while the person is standing on the right foot, in this example the second planting foot. While measurements are collected, a pressure map of the second planting foot 1701, in this case the right foot, may be displayed on the screen. It will be appreciated that foot order may be reversed, or only one foot might be measured.

Figure 17B:
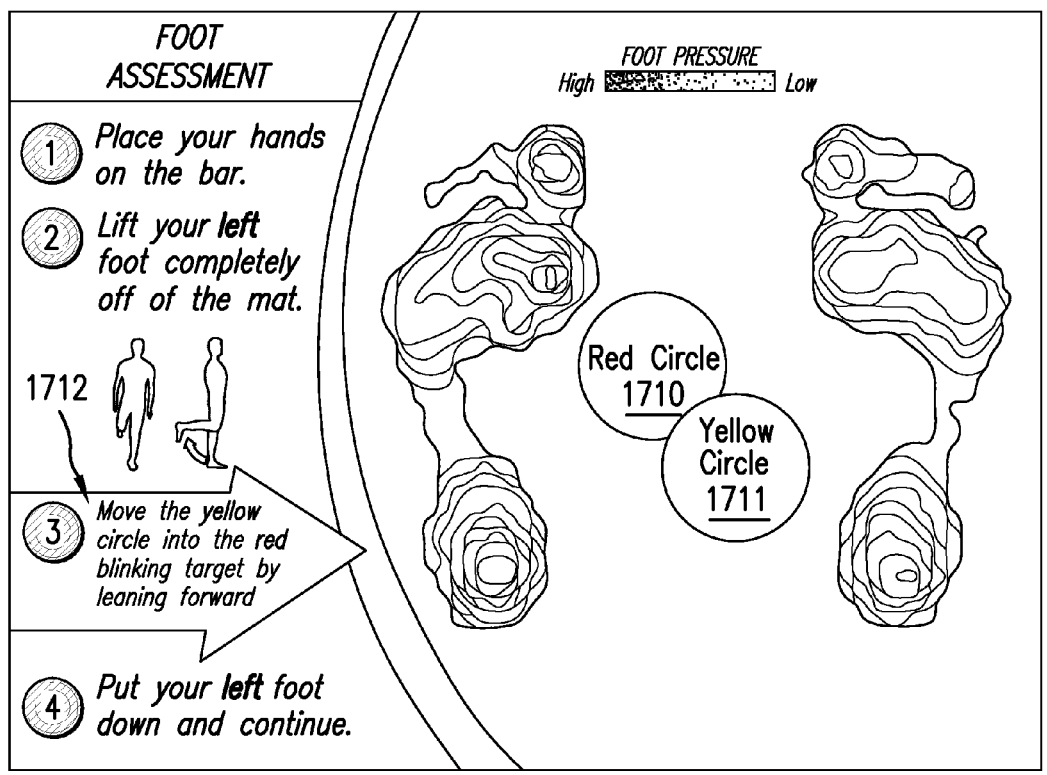
FIG. 17b illustrates an alternative example screen containing instructions that may be displayed to a person regarding taking pressure measurements of the person while the person stands on the right foot, according to an example embodiment of the present invention.

FIG. 17*b* illustrates an alternative example screen containing instructions that may be displayed to a person regarding taking pressure measurements of the person while the person stands on the right foot, according to an example embodiment of the present invention. Instructions for measuring on one foot 1712 may be displayed and highlighted. The person may be instructed to move a yellow circle 1710 into a red circle 1711 in order to balance the COF.

Figure 18:
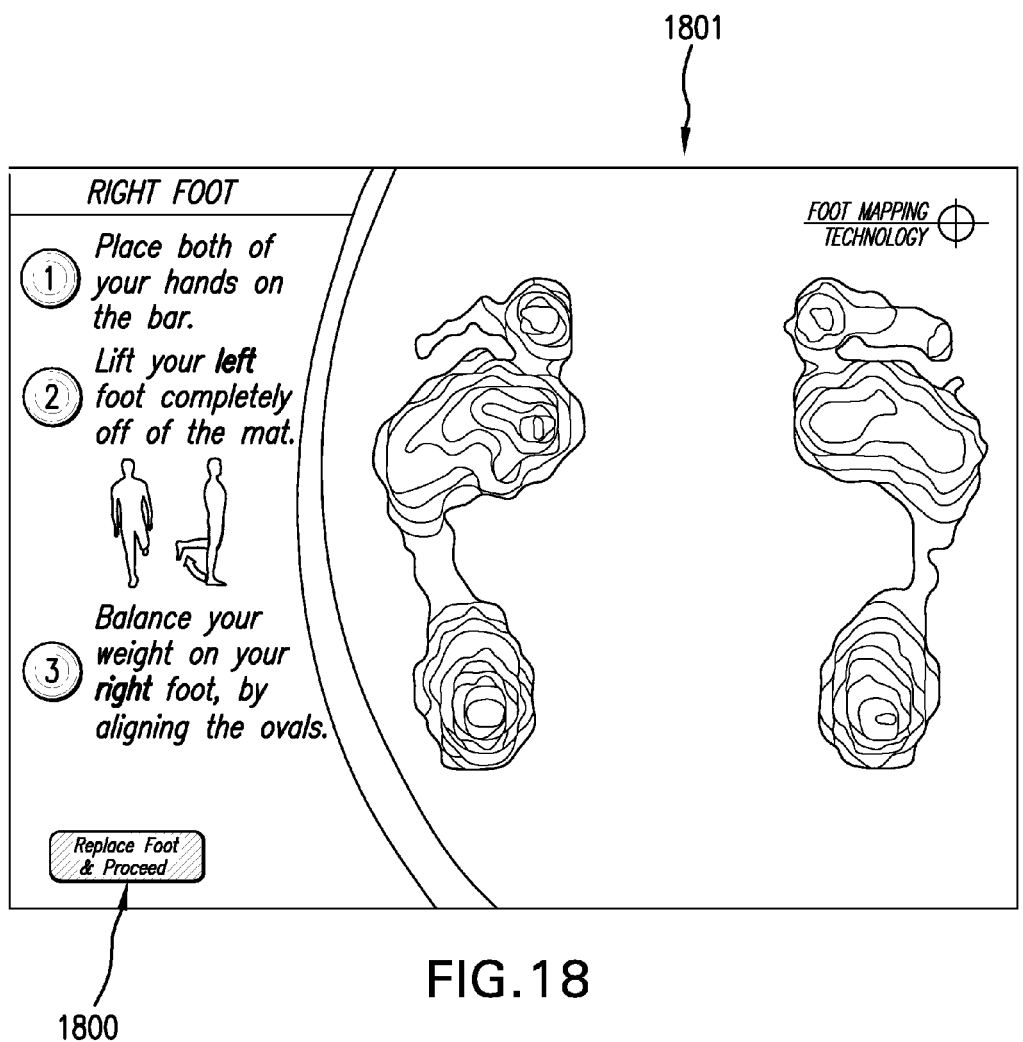
FIG. 18 illustrates an example screen that may be displayed after measurements of a single planting foot are taken, according to an example embodiment of the present invention.

FIG. 18 illustrates an example screen that may be displayed after measurements of a single planting foot are taken, according to an example embodiment of the present invention. This screen is similar to FIG. 16, although the instruction to replace the foot onto the pressure map may be integrated with an activated button 1800 instructing the person that he or she may proceed. This may be done according to example 710 in FIG. 7. A real-time pressure map 1801 of the feet may be displayed on the screen as the raised foot is placed back onto the pressure mat. When measurements have been completed and the person is ready to proceed, as indicated in pressing 1800, biomechanical data estimates may be calculated behind-the-scenes according to example 712 in FIG. 7.

Figure 19:
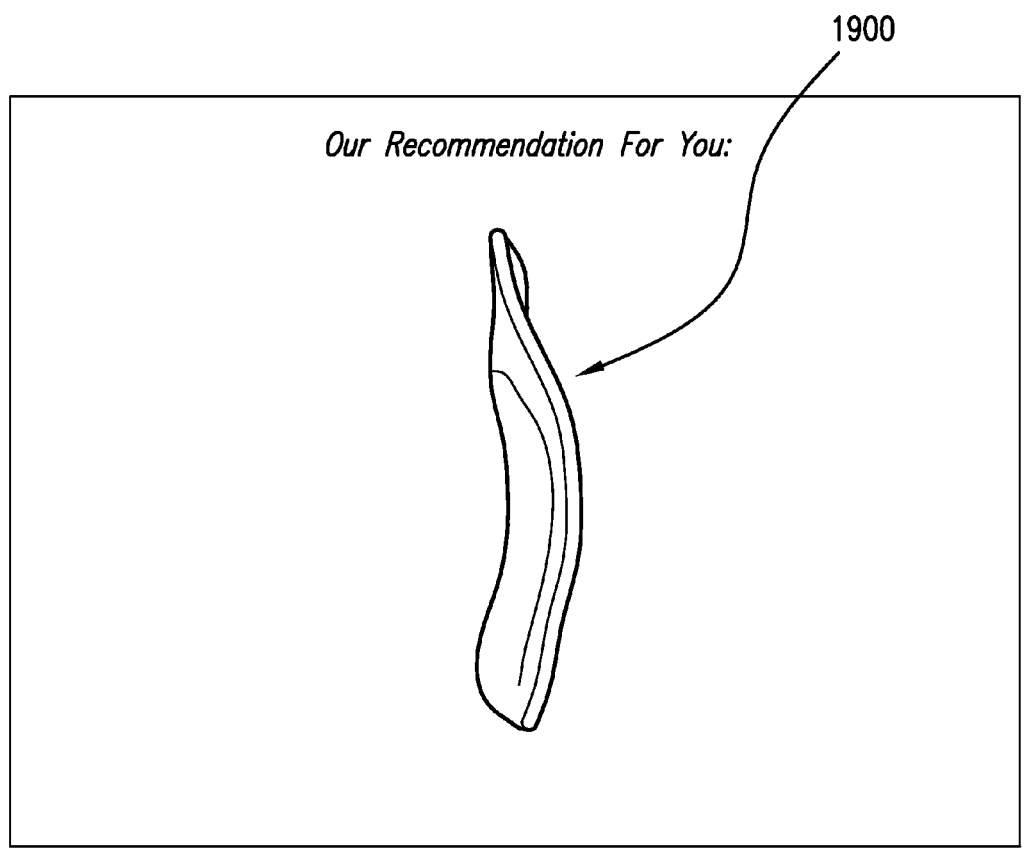
FIG. 19 illustrates an example screen that may display a selected recommended footcare product, in this example, an orthotic.

FIG. 19 illustrates an example screen that may display a selected recommended footcare product, in this example, an orthotic. An image 1900 of the footcare product may be displayed that a person may use to recognize the footcare product displayed in the merchandise display area, like that of 901 of FIG. 9. It may be appreciated that other indicia identifying a recommended footcare product may also be displayed, such as a rotating image, or an image that a person may manipulate through a touch screen, or a video clip containing an audio description, etc. It may be advantageous to color code various products so that a customer can more easily locate a recommended product.

Figure 20:
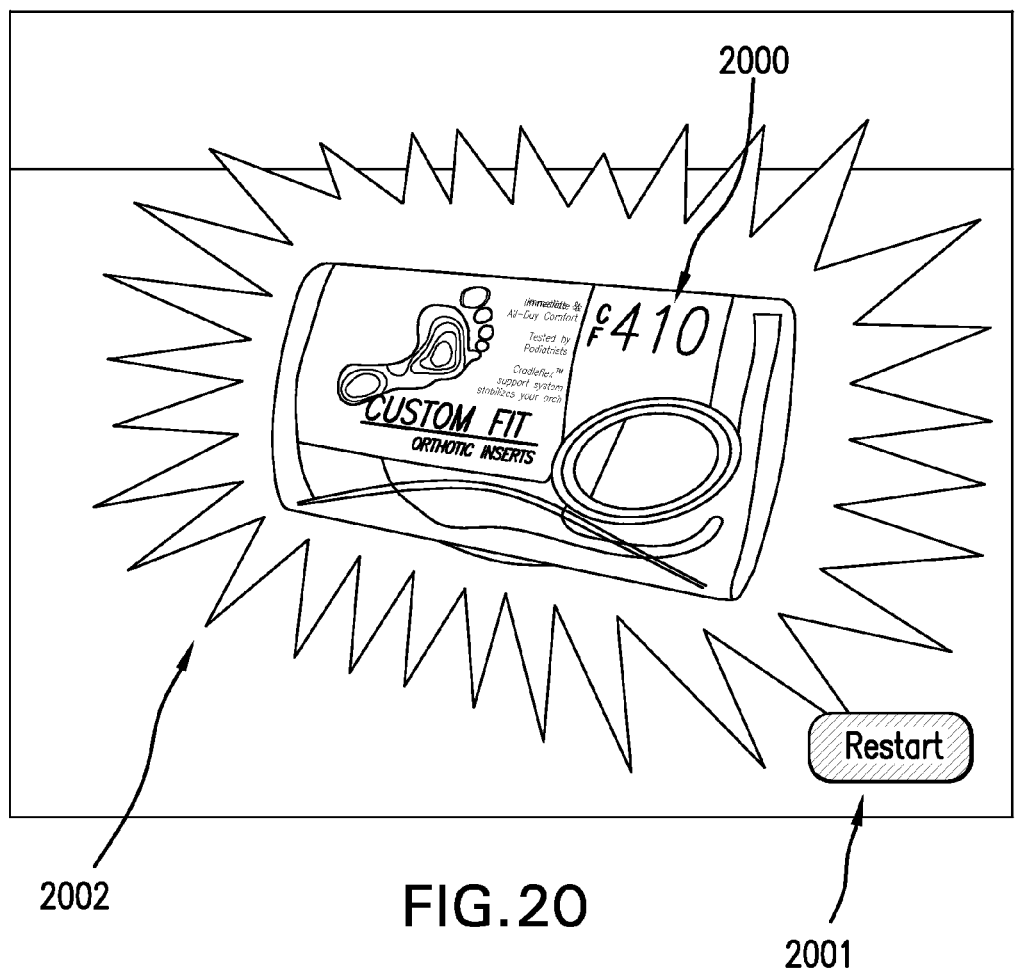
FIG. 20 illustrates an example screen displaying other information that may be displayed to a person, according to an example embodiment of the present invention.

FIG. 20 illustrates an example screen displaying other information that may be displayed to a person, according to an example embodiment of the present invention. For example, the screen may display further indicia of the recommended footcare product that was selected, such as a model number 2000. The packaging 2002 of the footcare product as it would appear on a merchandise display area 901, such as that of FIG. 9*a*, may also be displayed. A restart button 2001, in order to restart the selection process according to example 414 in FIG. 4, may be displayed to allow a person to restart the selection process, or so that another person waiting to use the kiosk may immediately start the process. Other information may also be displayed on the final screen, for example, any of the prior calculated biomechanical data estimates or pressure maps may be displayed. The person may be able to maneuver through various pages to view the person's own biomechanical data estimates.

In alternative embodiments, when the selection process is complete, the kiosk may display several recommended footcare products. The person may then, from these few selected footcare products, narrow the range of products down, either by eliminating the choices directly, or by answering a set of questions, such as comfort preferences, activities typically engaged in by the person, the particular activity that the footcare product may be used with, the type of shoe that the person may wear, or the type of socks that are worn. The footcare products may also be different types of products from which the user can choose. For example, the kiosk may display an assortment of orthotics and heel cups. In alternative embodiments, these preference choices may be asked prior to the last page and the kiosk may automatically eliminate choices for the person.

Several example embodiments of the present invention are specifically illustrated and described herein. However, it will be appreciated that modifications and variations of the present invention are covered by the above teachings and within the purview of the appended claims without departing from the spirit and intended scope of the invention.

What is claimed is:

1. A system comprising: a surface, wherein the surface is configured to allow a person to stand upon the surface; a plurality of pressure sensors located under the surface forming a 2-D array of sensors; a measurement system configured to obtain measurements from a customer's feet; a processor in communication with the plurality of pressure sensors, the processor configured to receive a plurality of pressure measurements from at least a subset of pressure sensors while the person stands upon the surface, the processor further configured to select a recommended footcare product from among a set of candidate footcare products based at least in part upon the plurality of pressure measurements, wherein the processor is configured to receive at least a first subset of the plurality of pressure measurements while the person stands stationary on one foot; an output device to display information received from the processor, the information identifying the recommended footcare product to the person; and a merchandise display area, the merchandise display area configured to display the set of candidate footcare products.

* * * * *